(12) United States Patent
Carlson et al.

(10) Patent No.: US 7,024,955 B2
(45) Date of Patent: Apr. 11, 2006

(54) METHODS AND SYSTEMS FOR DISSOLUTION TESTING

(75) Inventors: Eric D. Carlson, Cupertino, CA (US); Miroslav Petro, San Jose, CA (US); Son Hoai Nguyen, Santa Clara, CA (US)

(73) Assignee: Symyx Technologies, Inc., Santa Clara, CA (US)

( * ) Notice: Subject to any disclaimer, the term of this patent is extended or adjusted under 35 U.S.C. 154(b) by 0 days.

(21) Appl. No.: 10/414,185

(22) Filed: Apr. 14, 2003

(65) Prior Publication Data

US 2004/0168529 A1    Sep. 2, 2004

Related U.S. Application Data

(60) Provisional application No. 60/451,463, filed on Mar. 1, 2003.

(51) Int. Cl.
*G01N 33/15* (2006.01)
*G01N 33/00* (2006.01)

(52) U.S. Cl. ............... 73/866; 73/64.56; 73/864.25

(58) Field of Classification Search ............ 73/866, 73/64.56, 864.25; 702/23, 25, 30; 422/68.1, 422/81; 436/54, 178
See application file for complete search history.

(56) References Cited

U.S. PATENT DOCUMENTS

| | | | | |
|---|---|---|---|---|
| 3,846,075 | A * | 11/1974 | Cioffi | 422/81 |
| 4,279,860 | A * | 7/1981 | Smolen | 73/866 X |
| 4,335,438 | A * | 6/1982 | Smolen | 73/866 X |
| 4,429,584 | A | 2/1984 | Beyer et al. | 73/864.21 |
| 4,678,639 | A | 7/1987 | Dong et al. | 422/81 |
| 4,754,657 | A | 7/1988 | Schneider | 73/866 |
| 4,879,917 | A | 11/1989 | Eppelmann et al. | 73/866 |
| 4,924,716 | A * | 5/1990 | Schneider | 73/866 |
| 5,108,708 | A | 4/1992 | Hanus | 422/100 |
| 5,412,979 | A * | 5/1995 | Fassihi | 73/866 X |
| 5,604,132 | A | 2/1997 | Capuano et al. | 436/52 |
| 6,004,822 | A * | 12/1999 | Li et al. | 422/81 X |
| 6,060,024 | A | 5/2000 | Hutchins et al. | 422/81 |
| 6,174,497 | B1 | 1/2001 | Roinestad et al. | |
| 6,265,226 | B1 | 7/2001 | Petro et al. | |
| 6,271,038 | B1 | 8/2001 | Liu et al. | 436/161 |
| 6,280,772 | B1 * | 8/2001 | Pinkus | 424/486 |
| 6,461,515 | B1 | 10/2002 | Safir et al. | |
| 6,492,184 | B1 | 12/2002 | Petro et al. | |
| 6,558,957 | B1 | 5/2003 | Roinestad et al. | |
| 6,569,686 | B1 | 5/2003 | Avdeef et al. | |
| 6,764,651 | B1 * | 7/2004 | Fernando et al. | 422/82.06 |
| 6,799,123 | B1 * | 9/2004 | Hughes | 702/25 |
| 2002/0014485 | A1 | 2/2002 | Fernando et al. | 219/543 |
| 2002/0039750 | A1 | 4/2002 | Cole et al. | 435/7.1 |
| 2002/0048610 | A1 | 4/2002 | Cima et al. | 424/725 |

(Continued)

FOREIGN PATENT DOCUMENTS

EP    0 635 713    1/1995

(Continued)

OTHER PUBLICATIONS

Patent Cooperation Treaty International Search Report, European Patent Office, Patrick Wach, Oct. 19, 2004, International Application No. PCT/US2004/006054.

(Continued)

*Primary Examiner*—Thomas P. Noland

(57) ABSTRACT

Methods and systems for determining a dissolution profile of a sample material, and for solubilization screening of a library defined by an array comprising multiple sample materials are disclosed. The methods and systems are particularly advantageous for sampling and evaluation of very small samples, and can be advantageously applied in connection with evaluation of drug candidates.

73 Claims, 13 Drawing Sheets

U.S. PATENT DOCUMENTS

| | | |
|---|---|---|
| 2003/0080062 A1 | 5/2003 | Petro et al. |
| 2003/0087457 A1* | 5/2003 | Hughes ................. 422/68.1 X |
| 2003/0124028 A1* | 7/2003 | Carlson et al. ............ 422/68.1 |
| 2004/0076546 A1* | 4/2004 | Bissett ...................... 422/68.1 |
| 2004/0115822 A1* | 6/2004 | Schapaugh et al. ........... 436/91 |

FOREIGN PATENT DOCUMENTS

| | | |
|---|---|---|
| WO | WO 01/02834 | 1/2001 |
| WO | WO 01/16582 A1 | 3/2001 |
| WO | WO 200231477 A2 * | 4/2002 |
| WO | WO 200214377 A * | 8/2002 |
| WO | WO 03/014732 | 2/2003 |
| WO | WO 03/016883 A1 | 2/2003 |
| WO | WO 03/042694 A2 | 5/2003 |

OTHER PUBLICATIONS

Toher, "Monitoring Rapid-Release Sublingual Vitamin $B_{12}$ Tablets by in situ Fiber Optic Dissolution Technology", Delphian Tech Note, Apr. 10, 2003, No.: 00001-1, www.delphian-tech.com., 3 pages.

* cited by examiner

METHODS AND SYSTEMS FOR DISSOLUTION TESTING

RELATED APPLICATION

This application claims the benefit of and priority to co-owned U.S. provisional patent application Ser. No. 60/451,463 entitled "Novel Methods and Apparatus for Evaluating the Effects of Various Conditions on Drug Compositions Over Time" filed Mar. 1, 2003 by Carlson et al.

TECHNICAL FIELD

The present invention relates to the field of research for soluble forms of materials such as chemical compounds, with an emphasis in preferred embodiments on drug candidates. More particularly, the present invention is directed toward methods and systems for rapidly evaluating the time-dependent solubilization characteristics of materials such as chemical compounds (e.g., drug candidates). In particularly preferred embodiments, dissolution profiles are determined for libraries of sample materials such as drug candidates, where such libraries are prepared using high-throughput (i.e.,combinatorial) formulation protocols.

BACKGROUND OF THE INVENTION

This invention is directed at "dissolution" or "solubilization", each of which are used interchangeably herein to refer to a dynamic process—involving the kinetics by which a material dissolves into a given media (e.g., solvent). Viewed from the perspective of the resulting solution, dissolution can be characterized by the time-rate-of-change in concentration of the sample material in the solution over a dissolution period. In contrast, "solubility" generally refers to an equilibrium condition (e.g., a thermodynamic value) and particularly refers to how much of a sample material will dissolve in a given medium under conditions in which thermodynamic equilibrium is achieved. In general, materials that have a high solubility will generally demonstrate faster dissolution than materials of lower solubility. However, dissolution characteristics are not directly and specifically correlatable to solubility, and valuable information about materials can be obtained by looking at dissolution profiles (e.g., in addition to overall solubility data).

Dissolution testing of materials is typically practiced by dissolving at least a portion of a material in a solvent to form a solution that has a varying concentration of the material over a dissolution period. Aliquots of the solution are then taken at various times during the dissolution period, and the concentration of the material in aliquot is measured. This information, taken collectively, represents a time-dependent dissolution profile. If allowed enough material and enough time to dissolve to reach saturation, one could also measure solubility. However, a dissolution profile can be determined without necessarily determining solubility. Dissolution testing is known in many fields, but is of particular significance with respect to drug candidates.

Combinatorial chemistry has revolutionized the process of drug discovery. See, for example, 29 Ace. Chem. Res. 1–170 (1996); 97 Chem. Rev. 349–509 20 (1997); S. Borman, Chem. Eng. News 43–62 (Feb. 24, 1997); A. M. Thayer, Chem. Eng. News 57–64 (Feb. 12, 1996); N. Terret, 1 Drug Discovery Today 402 (1996). Combinatorial chemistry has also been applied to materials research more generally. See, for example, U.S. Pat. No. 6,004,617 (generally), U.S. Pat. No. 5,985,356 (inorganic materials), U.S. Pat. No. 6,420,179 (organometallic materials), U.S. Pat. No. 6,346,290 (polymer materials), and U.S. Pat. No. 6,410,331 (catalyst screening) to Schultz et al. See also U.S. Pat. No. 6,514,764 (catalyst screening) to Willson.

Although combinatorial chemistry has to a great extent eliminated the bottleneck in early drug discovery, other bottlenecks have emerged in getting a new drug to market. One such bottleneck is the identification of a drug candidate that is soluble and/or that has an appropriate rate of solubilization in an aqueous solution such as water or buffered water. Low solubility and/or solubilization of a drug candidate can be problematic because it can make the drug difficult to deliver effectively in a biological system. In fact, it has been estimated that as many as thirty percent (30%) of drug candidates are discarded because they are poorly soluble (e.g., soluble to less then ten milligram per milliliter (<10 mg/ml)) and/or have poor solubilization. Drug candidates are often sent back from animal toxicology and/or clinical trials because of inability to formulate them into an acceptable delivery form (e.g., a soluble form, with appropriate solubilization characteristics).

Approaches to solve solubility and/or solubilization problems include identification of salt forms or related structures (e.g., polymorphs) of the drug candidate that may show equivalent activity and improved solubility and/or solubilization. However, such methods of identification (involving, for example, design, synthesis, and characterization of salt and polymorphic forms of a drug candidate) are generally time consuming, tedious and are by themselves bottlenecks in getting a new drug to market.

Although efforts have been made to make certain aspects of such approaches more efficient (e.g., high-throughput investigation of drug-candidate polymorphs), the current state of the art has not adequately addressed a now-evident need for a high-throughput methods and systems for determining solubilization characteristics of materials such as drug candidates. Of particular relevance, traditional methods for dissolution testing are further disadvantaged in that the dissolution screening of materials comprising drug candidate compounds is generally done with a standard USP test equipment which requires a large volume of fluid (e.g., 900 ml per sample) and a large amount of sample (e.g., 100 mg to 200 mg). See, for example, U.S. Pat. No. 4,924,716 to Schneider. The disadvantage of such known dissolution testing methods and systems is particularly evident in light of the fact that combinatorial synthesis methods generally result in new drug candidate compounds being produced only in a limited quantity during the early stage of discovery and/or lead optimization.

Accordingly, there is a need in the art to provide reliable, reproducible, high-throughput, dissolution screening methods and systems that only require a small amount of test sample.

SUMMARY OF THE INVENTION

It is therefore an object of the present invention to provide reliable, reproducible, high-throughput, dissolution screening methods and systems that only require a small amount of sample material for testing or screening.

It is also an object of the invention to provide reliable systems for reproducibly sampling small amounts of materials.

Briefly, therefore, the present invention is generally directed to methods for determining a dissolution profile for a sample material.

In one embodiment of such methods for determining a dissolution profile, not more than about 100 mg, preferably not more than about 50 mg, and most preferably not more than about 20 mg of a sample material is combined with a solvent. At least a portion of the sample material is dissolved in the solvent over a period of time to form a solution, with the period of time defining a dissolution period. The solution has a concentration of the sample material that varies during the dissolution period. A portion of the solution is sampled successively in time at least twice, and preferably at least three times during the dissolution period. Specifically, the solution is sampled at a first time within the dissolution period to obtain a first aliquot of the solution, and at a later second time within the dissolution period to obtain a second aliquot of the solution. The concentration of the sample material in the first aliquot of the solution, and the concentration of the sample material in the second aliquot of the solution is then determined.

In another embodiment of such methods for determining a dissolution profile, at least a portion of a sample material is dissolved in a solvent over a period of time to form a solution, with the period of time defining a dissolution period. The solution has a concentration of the sample material that varies during the dissolution period. A portion of the solution is sampled successively in time at least twice, and preferably at least three times during the dissolution period. Specifically, the solution is sampled at a first time within the dissolution period to obtain a first aliquot of the solution, and at a later second time within the dissolution period to obtain a second aliquot of the solution. The difference between the first time and the second time is not more than about 2 minutes, preferably not more than 1 minute. The concentration of the sample material in the first aliquot of the solution, and the concentration of the sample material in the second aliquot of the solution is determined.

In a further embodiment of such methods for determining a dissolution profile, at least a portion of the sample material is dissolved in a solvent over a period of time to form a solution, with the period of time defining a dissolution period. The solution has a concentration of the sample material that varies during the dissolution period. A portion of the solution is sampled at least twice, and preferably at least three times during the dissolution period. Specifically, the solution is sampled at a first time within the dissolution period to obtain a first aliquot of the solution, and at a later second time within the dissolution period to obtain a second aliquot of the solution. In this embodiment, a portion of the first aliqout of the solution is further subsampled to obtain a first sub-aliquot of the solution, and then the concentration of the sample material in the first sub-aliquot of the solution is determined. Likewise, a portion of the second aliquot of the solution is further subsampled to obtain a second sub-aliquot of the solution, and the concentration of the sample material in the second sub-aliquot of the solution is determined.

In preferred protocols of the embodiment in the immediately-preceding paragraph, the step of subsampling to obtain the first sub-aliquot of the solution results in a remainder portion of the first aliquot, and the method further comprises returning the remainder portion of the first aliquot to the solution. In this case, the step of sampling at a second time to obtain the second aliquot of the solution is effected after the remainder portion of the first aliquot is returned to the solution. Also, the step of subsampling to obtain the second sub-aliquot of the solution results in a remainder portion of the second aliquot, and the method further comprises returning the remainder portion of the second aliquot to the solution.

In preferred protocols of the embodiment in the two immediately-preceding paragraphs, a first make-up aliquot of a liquid media is provided to the solution, where the first make-up aliquot has a volume about the same as the volume of the first sub-aliquot. Preferably, the first make-up aliquot is provided after sampling to obtain the first aliquot of the solution, and before sampling to obtain the second aliquot of the solution. Likewise, a second make-up aliquot of a liquid media is provided to the solution, with the second make-up aliquot having a volume about the same as the volume of the second sub-aliquot. Preferably, the second make-up aliquot being provided after sampling to obtain the second aliquot of the solution.

The invention is also generally directed to methods for generating data defining a dissolution profile for a sample material.

According to these methods, a dissolution profile is determined according to any of the methods described in connection with the aforementioned embodiments, and then a first data point of the dissolution profile is defined by associating the determined concentration in the first aliquot (or first sub-aliquot) with the first time. Likewise, a second data point of the dissolution profile is defined by associating the concentration determined in the second aliquot (or sub-aliquot) with the second time. Preferably, such association is effected using a microprocessor. The resulting data can be a data set that is preferably displayed on a graphical user interface in graphical or tabular form.

The invention is further generally directed to a system for determining a dissolution profile for a sample material.

The system comprises a sample container for dissolving at least a portion of the sample material in a solvent over a dissolution period of time to form a solution that has a concentration of the sample material that varies during the dissolution period. The system also comprises an automated sampling probe for sampling a portion of the solution at least twice during the dissolution period, the solution being sampled at first and second times within the dissolution period to obtain first and second aliquots of the solution, respectively. The sampling probe has a distal end positionable in fluid communication with the solution in the sample container, and has a proximate end, that is opposing the distal end and in fluid communication therewith. The sampling probe has one or more fluid cavities and can comprise conduits integrally formed in a unitary body or supported by the probe body for providing fluid communication between the distal end and the proximate end of the sampling probe. The system also comprises a sub-sampling device, which is preferably a sampling valve, in fluid communication with the proximate end of the sampling probe. The sub-sampling device is configured for subsampling a portion of each of the first and second aliquots of the solution to obtain first and second sub-aliquots of the solution. The system comprises as well an analytical unit for determining the concentration of the sample material in the first and second sub-aliquots of the solution. In another embodiment, the system further comprises an automated dispensing probe for providing the sample material to the container and/or for providing a make-up aliquot to the container. The dispensing probe and sampling probes are preferably under separate functional control from each other (allowing for independent dispensing and/or sampling therefrom), but may be structurally integrated through a common probe head, allowing for integrated positional control of the dispensing probe and the sampling probe.

The invention is also generally directed to a system for automated sampling of small volume liquid samples.

This system comprises a sample container for containing a liquid sample, and an automated liquid handing system comprising a sampling probe, a robotic arm for translating the sampling probe, and a pump in continuous or selectable fluid communication with the sampling probe for providing a motive force at least for withdrawing a portion of the liquid sample into the probe to effect sampling. The sampling probe has a distal end and a proximate end, with the distal end of the sample probe being positionable in fluid communication with the liquid sample in the sample container for sampling a portion of the liquid sample to obtain a sampled aliquot, and with the proximate end being opposing the distal end and in fluid communication therewith. The sampling probe has one or more fluid cavities and can comprise conduits integrally formed in a unitary probe body or supported by the probe body for providing fluid communication between the distal end and the proximate end of the sampling probe. A sampling valve provides fluid communication between the proximate end of the sampling probe and the pump. The sampling valve is a multi-port sampling valve comprising a sample loop, and the sampling valve is configured in at least a first selectable position and a second selectable position. The sampling valve is configured for loading at least part of the sampled aliquot into the sample loop through a sampling flow path from the proximate end of sampling probe to the first pump. The sampling valve is further configured for discharging the contents the sample loop from the sampling valve as a sub-aliquot of the sampled aliquot. In another embodiment, this system further comprises an automated dispensing probe for providing the sample material to the container and/or for providing a make-up aliquot to the container. The dispensing probe and sampling probes are preferably under separate functional control from each other (allowing for independent dispensing and/or sampling therefrom), but may be structurally integrated through a common probe head, allowing for integrated positional control of the dispensing probe and the sampling probe.

These inventions provide several advantages, particularly in connection with sampling of, and dissolution profiling of small amounts sample materials. These inventions are useful in many fields, including without limitation in characterization of materials in high-throughput or combinatorial workflows. In a preferred application, the inventions can be advantageously applied for evaluating dissolution characteristics of drug candidates or drug compositions.

Other features, objects and advantages of the present invention will be in part apparent to those skilled in art and in part pointed out hereinafter. All references cited in the instant specification are incorporated by reference for all purposes. Moreover, as the patent and non-patent literature relating to the subject matter disclosed and/or claimed herein is substantial, many relevant references are available to a skilled artisan that will provide further instruction with respect to such subject matter.

BRIEF DESCRIPTION OF THE DRAWINGS

The patent or application file contains at least one drawing executed in color. Copies of this patent or patent application publication with color drawings will be provided by the Office upon request and payment of the necessary fee.

DETAILED DESCRIPTION OF THE INVENTION

Figure 1:
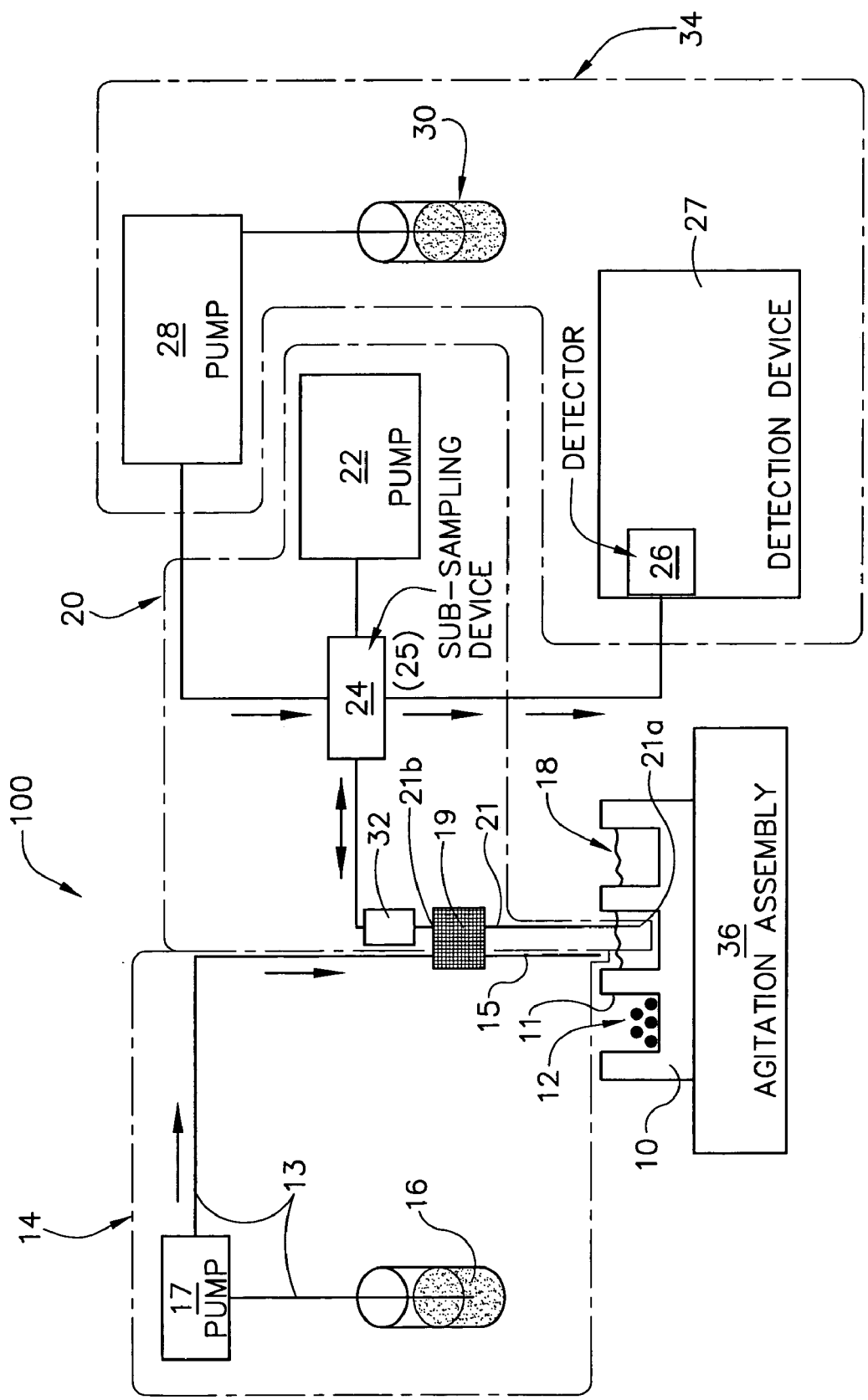
FIG. 1 shows a schematic of an illustrative high throughput solubility screening system in accordance with the principles of the present invention.

The invention as described and claimed herein generally includes methods for determining a dissolution profile of a sample material or of multiple sample materials that are members of an array or library. The invention also includes methods for generating data, such as a data set, for defining a dissolution profile of a sample material or of multiple sample materials that are members of an array or library. The invention includes as well, a system for determining a dissolution profile of a sample material or of multiple sample materials that are members of an array or library. In another aspect, the invention more generally includes a system for automated sampling of small volume liquid samples, or of multiple liquid samples that are members of an array or library. The particular nature of each of these aspects of the invention are described hereinafter.

Methods for Determining a Dissolution Profile

One aspect of the invention is directed toward methods for determining a dissolution profile of a sample material, or of multiple sample materials that are members of an array or library.

These methods generally comprise (i) dissolving at least a portion of the sample material in the solvent over a period of time to form a solution, where the period of time defines a dissolution period, and the solution has a concentration of the sample material that varies during the dissolution period, (ii) sampling a portion of the solution at least twice during the dissolution period, the solution being sampled at a first time within the dissolution period to obtain a first aliquot of the solution, and at a later second time within the dissolution period to obtain a second aliquot of the solution, and (iii) analyzing the first and second aliquots of the solution to determine the concentration of the sample material in the first aliquot of the solution, and to determine the concentration of the sample material in the second aliquot of the solution. The dissolving is preferably initiated by, and these methods can generally further comprise, (iv) combining an amount of the sample material with an amount of a liquid media (e.g., a solvent) into which the sample material will dissolve. In preferred embodiments, the solution is preferably sampled at least three times during the dissolution period, such that the method as described further comprises sampling a portion of the solution at a later third time within the dissolution period to obtain a third aliquot of the solution, and analyzing the third aliquot to determine the concentration of the sample material in the third aliquot of the solution.

These methods are particularly characterized by one or more of the following features (A–M), considered alone or in combination in each and every possible permutation. Generally considered, the characterizing features of the invention include:

(A) the type of sample material (e.g. drug candidate);

(B) the relatively small amount (e.g. weight) of the sample material (e.g., not more than about 50 mg);

(C) the relatively small amount (e.g., volume) of the media (e.g., solvent) with which the sample material is combined to initiate dissolution (e.g., not more than about 50 ml);

(D) the protocols (including specific methods and/or devices) by which dissolution is initiated and initial sampling is effected (e.g., sampling the first aliquot from the solution within a very short period of time, such as not more than about 1 minute, after initiation of dissolution);

(E) the protocols (including specific methods and/or devices) by which sampling is effected to obtain an accurate, small volume sample (e.g., sampling at least a portion of the solution to obtain an aliquot of the solution, and then subsampling a portion of the sampled aliquot to obtain sub-aliquot of the solution), where the sub-aliquot can then be analyzed to determine the concentration of the sample material in the solution;

(F) the protocols (including specific methods and/or devices) by which the amount of solution being sampled is preserved to allow for multiple samples even from a relatively small starting volume (e.g., by, in addition to sampling and subsampling protocols as described above, the combination of returning the remainder portion of the aliquot (the portion of the aliquot not included within the sub-aliquot) to the solution (e.g. to the container holding the solution);

(G) the protocols (including specific methods and/or devices) by which the total volume of the solution being sampled is substantially preserved to allow for more direct comparison of determined concentration values for multiple samples (e.g., by, independently, or in addition to the sampling and subsampling and/or remainder-returning protocols as described above, providing a make-up aliquot of a liquid media (e.g. the solvent) to the solution);

(H) the protocols (including specific methods and/or devices) for maintaining a dispersion formed by combining a solid sample material with a solvent, the dispersion comprising the solution being sampled and the undissolved solid sample material dispersed in the solution (e.g., through agitation); and (I) the protocols (including specific methods and/or devices) for sampling the solution of a dispersion, while allowing the undissolved sample material to remain in the dispersion (rather than being sampled off with the solution) (e.g., filtering of the sampled aliquots during or after sampling, preferably with back-flushing of the filter media so that undissolved solid sample material remains exposed to the solvent for continued dissolution into the solution).

(J) the relatively fast sampling frequency defined by the difference in time between sampling of successive aliquots (e.g., the difference between the first time and the later second time at which the first aliquot and the second aliquot are sampled, respectively) (e.g., the sampling frequency being not more than about 1 minute);

(K) the protocols (including specific methods and/or devices) that define a sampling plan for efficient sampling, particularly for efficiently sampling multiple members of an array of sample materials (e.g., a sampling plan that includes for each sample, sampling the solution at least six times over at least two distinct sampling intervals, including a first sampling interval proximate to the initiation of dissolution that involves sampling the solution at least three times, and a later-in-time second sampling interval separated substantially from the first sampling interval that also involves sampling the solution at least three times);

(L) the protocols (including specific methods and/or devices) by which these methods can be used to obtain a dissolution profile that is representative of dissolution in a dynamic environment, such as would mimic the environment along various regions of the gastrointestinal tract (e.g., by varying, and preferably controllably varying, a property, such as pH, of the solvent over time);

(M) the protocols (including specific methods and/or devices) by which these methods can be applied to a high-throughput method for evaluating a library or an array of sample materials, (e.g., an array comprising multiple members of sample materials in containers formed on or supported by a common substrate);

Because the invention is contemplated and is defined with respect to each and every possible combination and permutation of these characterizing features (A–M), a person of skill in the art would readily appreciate, for example, that these methods of the invention can be defined by the above-recited general steps (i), (ii) and (iii), and optionally (iv), in combination with one or more of features A–M. As a non-limiting example, these methods of the invention can be characterized by the combination feature A plus any one or more of the features B, C, D, E, F, G, H, I, J, K, L and M, the combination of feature B plus any one or more of features C, D, E, F, G, H, I, J, K, L and M, the combination of feature C plus any one or more of features D, E, F, G, H, I, J, K, L and M, the combination of feature D plus any one or more of features E, F, G, H, I, J, K, L and M, the combination of feature E plus any one or more of features F, G, H, I, J, K, L and M, the combination of feature F plus any one or more of features G, H, I, J, K, L and M, the combination of feature G plus any one or more of features H, I, J, K, L and M, the combination of feature H plus any one or more of features I, J, K, L and M, the combination of feature I plus any one or more of features J, K, L and M, the combination of feature J plus any one or more of features K, L and M, the combination of feature K with any one or more of features L and M, and the combination of feature L with feature M.

In particularly preferred embodiments, the invention is defined by the general steps characterized by many of the features A-M in combination, including for example features B, D, E, F and J together in combination with each other, and optionally in further combination with one or more of the other features A, C, G, H, I, K, L and M.

Methods for Generating Data for Defining a Dissolution Profile

Another aspect of the invention includes methods for generating data, such as a data set, for defining a dissolution profile of a sample material or of multiple sample materials that are members of an array or library.

Generally, such methods comprise the general steps (i), (ii) and (iii), and optionally (iv) as described above in connection with the methods for determining a dissolution profile of a sample material (or of multiple sample materials that are members of an array or library), as supplemented herein. These methods further comprise associating the determined concentration of the sample material in particular aliquots with the particular respective times at which such aliquots were taken (e.g., associating the determined concentration of the sample material in the first aliquot with the first time to define a first data point of the dissolution profile, and associating the determined concentration of the sample material in the second aliquot with the second time to define a second data point of the dissolution profile). Preferably, such association is implemented with a microprocessor such as a personal computer. Preferably, the generated data, such as a data set, is stored in a memory device. Preferably, the generated data, such as a data set, can be retrieved from memory, for example, for being displayed on a graphical user interface.

Additionally, these methods are also particularly characterized by one or more of the aforementioned features (A–M), considered alone or in combination in each and every possible permutation, with preferred combinations and permutations as described above.

System for Determining a Dissolution Profile

In another aspect, the invention includes systems for determining a dissolution profile of a sample material or of multiple sample materials that are members of an array or library.

These systems generally comprise (i) a sample container for dissolving at least a portion of the sample material in a solvent over a dissolution period of time to form a solution that has a concentration of the sample material that varies during the dissolution period, (ii) an automated sampling probe for sampling a portion of the solution at least twice during the dissolution period, the solution being sampled at first and second times within the dissolution period to obtain first and second aliquots of the solution, respectively, and (iii) an analytical unit for determining the concentration of the sample material in the first and second sub-aliquots of the solution. Generally, such systems preferably also comprise a microprocessor, most preferably together with automation software for controlling the sampling probe, and a control system and software for controlling the analytical unit.

Additionally, these systems are also particularly characterized by one or more of features A and B (with respect to defining a fill level of a container or a container maximum fill volume), and/or by one or more of the features D, E, F, G, H and I, as described generally above and in more detail below. In a specific, non-limiting example, the sampling probe can comprise a distal end positionable in fluid communication with the solution in the sample container, and a proximate end in fluid communication with a subsampling device, in which the sub-sampling device is configured for subsampling a portion of each of the first and second aliquots of the solution to obtain first and second sub-aliquots of the solution. These systems are further particularly characterized by a control system (including software) effective for implementing one or more of the aforementioned features J and K, L and M. Such characterizing features form a defining part of the systems of the invention considered alone or in combination in each and every possible permutation, with preferred combinations and permutations as described above.

Systems for Automated Sampling of Small Volume Liquid Samples

A further aspect of the invention involves systems for automated sampling of small-volume liquid samples, or of multiple liquid samples that are members of an array or library.

These systems generally comprise (i) a sample container for containing a liquid sample, (ii) an automated liquid handing system comprising a sampling probe, a robotic arm for translating the sampling probe, and a pump in fluid communication with the sampling probe for providing a motive force at least for withdrawing a portion of the liquid sample into the probe to effect sampling, where the sampling probe has a distal end and a proximate end, the distal end of the sample probe being positionable in fluid communication with the liquid sample in the sample container for sampling a portion of the liquid sample to obtain an sampled aliquot, and (iii) a sampling valve providing fluid communication between the proximate end of the sampling probe and the pump, where the sampling valve is a multi-port sampling valve comprising a sample loop, the sampling valve is configured for loading at least part of the sampled aliquot into the sample loop through a sampling flow path from the proximate end of sampling probe to the first pump, and the sampling valve is further configured for discharging the contents the sample loop from the sampling valve as a sub-aliquot of the sampled aliquot.

Additionally, these systems are also particularly characterized by one or more of features A and B (with respect to defining a fill level of a container or a container maximum fill volume), and/or by one or more of the features D, E, F, G, H and I, as described generally above and in more detail below. These systems are further particularly characterized by a control system (including software) effective for implementing one or more of the aforementioned features J and K, L and M. Such characterizing features form a defining part of the systems of the invention considered alone or in combination in each and every possible permutation, with preferred combinations and permutations as described above.

Such systems can be employed in a number of applications for which it is desirable to enjoy the advantages of the present invention, especially in connection with automated sampling of small-volume liquid samples, or of multiple small-volume liquid samples that are members of an array or library. For example, one could apply this system for evaluating compound stability and/or excipient compatability of drug candidates, especially in drug compositions. In a preferred such application that is an alternative to dissolution testing, such systems can be employed in screening systems such as those described in co-owned, co-pending application U.S. Serial No. 60/451,463 entitled "Novel Methods and Apparatus for Evaluating the Effects of Various Conditions on Drug Compositions Over Time" filed Mar. 1, 2003 by Carlson et al., which is hereby incorporated by reference for all purposes.

Further Characterizing Features

More specific aspects of the various steps of the methods and of various components of the systems, and in particular, more specific aspects of each of the aforedescribed characterizing features (A–M) are described hereinafter. Such description includes more specific protocols (including specific methods and/or devices) for effecting such steps and for realizing such features. Since each of these more specific aspects more specifically define the general features outlined above, each of these more specific aspects are also characterizing features of the methods and the systems of the invention, considered alone or in combination in each and every possible permutation.

Sample Materials (Feature A)

As used herein, a sample refers to a single, discrete, individual unit of a material that is being evaluated. The sample material is an element, compound or composition being evaluated or tested or screened, for which a time variation in a property thereof is being determined, including for example in a preferred application, for which the dissolution profile is to be determined. The sample material can comprise or consist essentially of an organic material, an inorganic material, an organometallic material, or a combination thereof. The sample material can comprise or consist essentially of a polymer (e.g. a biological polymer or a non-biological polymer), or a composite material.

Preferred organic materials include small organic compounds (e.g. pharmaceuticals, agrichemicals, etc.) or biological polymers (e.g., nucleic acid polymers such as oligonucleotides, deoxyribonucleic acid polymers (DNA), ribonucleic acid polymers (RNA), etc., and amino acid polymers such as peptides, proteins, enzymes, etc.).

In some preferred embodiments, the sample material is a drug sample. A drug sample refers to a sample that is a drug candidate, a combination of drug candidates, or a drug composition. A drug composition refers to a composition that has one or more drug candidates and at least one excipient. Hence, the sample material preferably comprises or consists essentially of a drug candidate. A drug candidate is a compound (salt or neutral) shown under one or more various assays to have pharmacological (prophylactic or therapeutic) activity. A drug candidate may also be, but has not necessarily been, also shown to be safe under various toxicity assays. An active pharmaceutical ingredient (API) is a specific compound (salt or neutral), typically that has been approved by a governmental entity for use in a pharmaceutical, e.g., has been demonstrated to be, and is typically approved by a governmental entity (e.g., U.S. Food and Drug Administration) to be safe and effective for a particular indication. The methods and systems described in this patent application are preferred for use in evaluating sample materials that are drug candidates, which may or may hot be APLs. And, as those of skill in the art will appreciate, the exact API or drug candidate is not critical to this invention, but is typically a small organic molecule. In some cases, the drug candidate or API can be a biological polymer such as an oligonucleotide, a DNA, a RNA, a cDNA, a polypeptide or a protein. Some drug candidates have salts that are anionic or cationic and some drug candidates are neutrals. No matter the form, drug candidates may have different crystallographic polymorphs. Herein, the term polymorph is intended to include polymorphs, pseudo-polymorphs, hydrates, solvates and the like. The term excipient refers to a drug composition component that is typically intended to aid in manufacture, administration, absorption, appearance enhancement or retention of quality of a drug. Excipients rarely, if ever, possess pharmacological activity by themselves, and are accordingly loosely characterized as being substantially "inert." However, excipients can initiate, propagate or participate in chemical or physical interactions with a drug candidate, possibly leading to compromised or enhanced quality or performance of the drug. One example of an excipient that is commonly used is a solvent. For example, solvents may have an effect on the reaction rate of a drug candidate, or the degradation rate of a drug may change with the dielectric constant of the medium. As a specific example, certain studies have shown an increase in photo stability of Vitamin-B12 by the addition of viscogens such as glycerol or Ficoll. See Rong, Lui (editor), *Water-insoluble Drug Formulation*, Chapter 7 "Solubilizatinon Using CoSolvent Approach", J. Trivedi and M. Wells (authors), Interpharm Press, 2000, pp. 141–168, which is hereby incorporated by reference. One or more excipients used together with one or more drug candidates in a drug composition, can have a significant effect on dissolution of a drug composition sample material, and therefore, on the bioavailability of such drug sample.

The particularly physical state or form of the sample material is not narrowly critical to the invention. The sample material, such as a drug candidate or a drug composition, can take any form, such as a liquid, a solid, a gel, and the like. In preferred embodiments, the sample material is in the form of a solid, such as a crystalline solid. Crystalline solids can be single crystals or polycrystalline. The sample material can, in some embodiments, be provided for evaluation already in a partially dissolved state, including for example, as a suspension or dispersion (including both uniform and non-uniform dispersions), or as a solid-liquid emulsion. A dispersion, for example, can comprise a partially dissolved solid sample material dispersed in a solution—that is, dispersed in a liquid media into which the solid sample material is dissolving. In preferred embodiments, the sample material is provided as a substantially uniform dispersion, or is provided as a solid and combined with a solvent to form a substantially uniform dispersion.

Amount of Sample Materials (Feature B)

The amount of sample material being evaluated or tested or screened is not critical to many embodiments of the invention, but as noted above, the invention offers particular advantages with respect to methods and systems for evaluating or testing or screening relatively small amounts (e.g. weight) of sample materials. Hence, in preferred embodiments, the amount of sample material provided to a sample container is preferably not more than about 100 mg, more preferably not more than about 50 mg, and most preferably not more than about 20 mg. Generally, the amount of sample material can also be characterized as being not more than about 10 mg, not more than about 5 mg, not more than about 2 mg, or not more than about 1 mg. Also, for some applications, such as for combinatorial (high-throughput) screening of formulations such as drug compositions, the amount of sample material can be characterized as being not more than about 500 ug (0.5 mg), or not more than about 100 ug (0.1 mg), or not more than about 10 ug (0.01 mg) or not more than about 1 ug (0.001 mg). As used in the context of the amount of sample material, the term "about" refers to a degree of error associated with the type of instrument (e.g. weighing scale) used to determine the amount, based on a statistically significant and statistically acceptable basis for determining such error.

Solvent/Amount of Solvent (Feature C)

The solvent generally refers to the liquid media into which the sample material is dissolved during the dissolution test. The particular type of liquid media used in connection with the methods of this invention is not narrowly critical, and can be selected based on the type of sample material being investigated. Generally, the liquid media can be a solvent having a single unitary chemical composition (e.g., substantially pure solvents consisting essentially of one type of solvent, such as water, ethanol, etc.) or can be a solvent having a combination of chemical compositions (e.g., co-solvents comprising two or more miscible or imiscible solvents, such as water/ethanol co-solvents). The solvent can generally include one or more components or agents for controlling ionic strength (e.g., different salts or concentrations of salts), pH, pOH, or one or more agents or components that are solubilizers, disintegrants, or surfactants.

In some preferred applications, such as applications for evaluating dissolution of drug candidates, the liquid media can be water or an aqueous media, such as a buffered aqueous media, including without limitation buffered solutions having a pH ranging from about 2 to about 10, preferably from about 2 to about 4, from about 3 to about 5, from about 4 to about 7, from about 6 to about 8, from about 6 to about 9, or from about 7 to about 10. The liquid media used as the solvent can also be biological fluids (e.g., blood, saliva, gastric fluid), or mimics of such fluids (e.g., artificial blood or artificial saliva, etc.).

The amount of solvent combined with the sample material in the sample container for evaluation is not critical to many embodiments of the invention. Generally, the sample material is combined with an amount of solvent effective for forming a solution having a detectable concentration of sample material in the solution. As such, a person of skill in the art will appreciate that the amount of solvent to be combined with the sample material can be determined based on the type of sample material, the amount of the sample material, and the sensitivity of the analytical unit or system. In one general approach, the amount of solvent can be controlled to obtain a concentration of the sample material in solution that provides for non-equilibrium (e.g., with respect to dissolution, non-saturation) conditions (sometimes referred to as "sink" conditions) during the evaluation period. For example, the amount of solvent can be controlled to obtain a concentration of the sample material in solution that is within the range of about 5% to about 25% of the equilibrium solubility, preferably from about 10% to about 20% of the equilibrium solubility, in each case of that sample material in that solvent at the test temperature of interest.

In some preferred applications, such as applications for evaluating dissolution of drug candidates, the sample material is combined with an amount of solvent effective for forming a solution having a concentration of sample material in the solution ranging from about 0.01 mg/ml to about 10 mg/ml, preferably from about 0.1 mg/ml to about 5 mg/ml. As a non-limiting example, an amount of sample material ranging from 0.01 mg to 0.5 mg is combined with an amount of solvent ranging from 1 ml to 10 ml. As further non-limiting examples, the sample material (e.g., a drug candidate-containing sample) can be combined with a solvent with the following relative amounts: not more than about 100 mg of sample material with not more than about 100 ml of solvent; not more than about 50 mg of sample material with not more than about 50 ml of solvent; not more than about 20 mg of sample material with not more than about 20 ml of solvent; not more than about 10 mg of sample material with not more than about 10 ml of solvent; not more than about 5 mg of sample material with not more than about 5 ml of solvent; not more than about 2 mg of sample material with not more than about 2 ml of solvent; not more than about 1 mg of sample material with not more than about 1 ml of solvent; not more than about 0.1 mg of sample material with not more than about 0.1 ml of solvent; and not more than about 0.01 mg of sample material with not more than about 0.01 ml of solvent.

As noted above, the invention offers particular advantages with respect to methods and systems for evaluating or testing or screening relatively small amounts (e.g. weight) of sample materials, and also for evaluating such sample materials in relative small volumes of solution. Hence, in preferred embodiments, the total amount of solvent to be combined with the sample material in a sample container (and substantially correspondingly, the total amount of the resulting solution—e.g., of a dispersion comprising the solution and undissolved solid sample material that is formed from the combination of a solvent and a solid sample material) is preferably not more than about 100 ml, more preferably not more than about 50 ml, and most preferably not more than 20 ml. In many applications, it will be preferred to be a total solution volume of not more than about 10 ml, or not more than about 5 ml, or not more than about 2 ml, or not more than about 1 ml, or not more than about 0.5 ml or not more than about 0.1 ml. Preferably, such total amount of solvent ranges from about 0.1 ml to about 50 ml, preferably from about 0.5 ml to about 20 ml, and most preferably from about 1 ml to about 10 ml or from about 2 ml to about 5 ml.

As used in the context of the amount of solvent or the amount of total solution, the term "about" refers to a degree of error associated with the type of instrument (e.g. volumetric measure) used to determine the amount, based on a statistically significant and statistically acceptable basis for determining such error.

Initiation of Dissolution and Initial Sampling (Feature D)

Dissolution is initiated by combining the sample material a solvent, preferably with a suitable solvent, and preferably under conditions (e.g., temperature) effective for causing at least a portion of the sample material to dissolve in the solvent. The sample material and solvent can be combined in a container such as a sample container. The order of addition is not critical to the invention, and can include adding the solvent to the contained sample material, or adding the sample material to the contained solvent. In some preferred approaches, the sample material is provided to the container first, and then the solvent is added to the contained sample material.

The type of container is not critical to the invention. The container can be an individual container, such as a vial, beaker, test-tube, flask, etc. For many applications, including for example for combinatorial or high-throughput applications (described more fully below), an array of multiple sample materials are contained in multiple containers, respectively, with each sample material in its own discrete, dedicated container. In such cases, the containers can be structurally integrated, such as being formed in or supported by a common substrate. Hence, for example, the containers can be wells of a microtiter plate, or can be individual vials supported in wells of a microtiter plate. Standard microtiter formats (typically having a 0.9 mm center-to-center distance between adjacent wells or vials—that is, a 0.9 mm "pitch"), and typically in an 8 row by 12 column (or vice-versa) format, that is an "8×12 format", is particular useful for performing high throughput reaction and screening of samples. Another preferred format for slightly larger volume containers is a ninety-six well plate in an 8×12 format with about a 20 mm pitch (center-to-center distance of adjacent wells or vials). Other microtiter formats can also be employed, including 384-well plates. In general, the number of containers (e.g., vials or wells) can be 96×N, where N ranges from 1 to about 20, and preferably from 1 to 5. The containers can be open during the dissolution process, or can be sealed, such as hermetically sealed, during the dissolution process, and can be isolated from each other (e.g., to avoid cross-contamination between adjacent containers). The containers can be of any suitable material, including for example glass, plastic, metal, etc. Metals such as aluminum are preferred in some embodiments (e.g., for control of thermal properties of the solution).

The sample material is combined with the solvent at an initiation time, $t_o$, to initiate dissolution of the sample material in the solvent. In preferred protocols, the dissolution profile is characterized very early in the dissolution period—to provide valuable information about the kinetics of the initial part of the dissolution process. Accordingly, the first and second aliquots of the solution are preferably sampled as soon as practical after the initiation of dissolution, and particularly, within the initial interval of time that includes the fastest dissolution rate (i.e., the highest time-rate-of-change of concentration of the sample material in the solution). In preferred embodiments, the solution is sampled at least three times during the dissolution period, with each of the first, second and third aliquots being sampled as soon as practical after the initiation time, and particularly, within the interval of time that includes the fastest dissolution rate.

More specifically, in some applications, the first time at which the solution is sampled to obtain the first aliquot is within about 1 minute after the initiation time, $t_o$. Preferably in some cases, the first time at which the solution is sampled to obtain the first aliquot is within about 30 seconds after the initiation time, $t_o$, within about 10 seconds after the initiation time, $t_o$, or within about 5 seconds after the initiation time, $t_o$, or within about 2 seconds after the initiation time, $t_o$. The sampling frequency for the subsequent second sampling, defined by the difference in time between the first time and the second time, is preferably not more than about 1 minute. Likewise, where a subsequent third sample is done to obtain a third aliquot of the solution as part of the initial set of sampling, the sampling frequency for the third sampling, defined by the difference in time between the second time and the third time, is also preferably not more than about 1 minute. Hence, it can be appreciated that the a first sampling interval comprising the first time, the second time, and preferably also the third time is preferably initiated directly after and proximate to the initiation time, and at any rate, the first sampling interval can be completed with two samples in not more than about 2 minutes total, and with three samples with not more than about 3 minutes total, to obtain kinetic information about the onset of dissolution. More specifically preferred sampling frequencies are discussed below (in connection with Feature J), and such preferred sampling frequencies are particularly applicable to the present discussion as well.

The above description details the methodologies by which dissolution is initiated, by which initial sampling is effected (e.g., sampling the first aliquot from the solution) within a very short period of time after initiation of dissolution, and by which a dissolution profile is obtained for a first sampling interval that is proximate in time to the initiation of dissolution. Such methodologies can be advantageously effected using the system described below in connection with the preferred embodiments of the invention.

In particular, such methodologies can be effected using, in combination, an automated dispensing probe for providing either or both of the sample material and/or the solvent to the container (e.g., at the initiation time, $t_o$), and an automated sampling probe for sampling the solution to obtain the first and second aliquots of the solution during the dissolution period.

The automated dispensing probe can be a component of an automated solid (e.g., powder) dispenser, such as the Powderinium (Autodose, S.A., Geneva, Switzerland) or of an automated liquid dispenser, such as the Cavro (Tecan Scientific Instruments, San Jose, Calif.). Automated solid dispensers can further comprise a robotic arm for translating the automated dispensing probe for positioning, a hopper or other source container for the material to be dispensed, and automation software for controlling the dispenser. Automated liquid dispenser can be an automated liquid handing robot that further comprises a robotic arm for translating the automated dispensing probe for positioning, a source container for the solvent or sample material to be dispensed, a pump in fluid communication with the dispensing probe for providing a motive force for dispensing, for example the solvent, into the container, and automation software for controlling the dispenser.

The automated sampling probe can have a distal end positionable in fluid communication with the solution in the container for sampling the solution during the dissolution period. The automated sampling probe is preferably a component of an automated liquid handing unit or system, with the liquid-handling unit or system further comprising a robotic arm for translating the automated sampling probe for positioning, a pump in fluid communication with the sampling probe for providing a motive force for withdrawing a portion of the solution into the probe to effect sampling, and automation software for controlling the sampling probe.

The dispensing probe and the sampling probe can be structurally independent of each other, or can be structurally integrated with each other (e.g., using a common probe head that supports each of the dispensing probe and the sampling probe). In either case, the function of the dispensing probe and the function of the sampling probe can controlled independently of each other. That is, the functionality of, and the control of the functionality of, at least the dispensing function of the dispensing probe and the sampling function of the sampling probe is independent of each other, such that dispensing of sample material or solvent can occur at the same time, or in close temporal proximity to sampling to obtain the first aliquot of the solution. The independence of the control goes towards being able to effectively coordinate the timing of such functionality, and does not necessarily imply that there is no control communication between the two devices. For example, it may be desirable to have independently-controlled devices in which the control signal for initiating the initial sampling with the sampling probe is triggered by a signal from the dispensing probe indicating that the dispensing has begun (and that therefore, dissolution has been initiated). Further, the automation software for these devices is can be separate, or can be partially or totally integrated.

Sampling, Subsampling and Returning of Remainder Portion (Features E, F)

In a preferred protocol, a portion of each of the sampled aliquots of the solution (e.g., the first aliquot and the second aliquot) are subsampled to obtain corresponding sub-aliquots (e.g., a first sub-aliquot from the first aliquot and a second sub-aliquot from the second aliquot) of the solution. The subsampling refers to a further sampling of a portion of the original sample withdrawn from the solution in the container (the original sampled aliquot) to obtain a sub-aliquot that represents a smaller portion (e.g., smaller volume) than the volume of the original aliquot withdrawn from the container. Such subsampling offers several advantages over a direct sampling approach in which a very small volume is withdrawn in the first instance directly from the container. First, such subsampling allows for a larger initial sample size to be withdrawn, which may be more representative of the bulk or physically-averaged properties (e.g. concentration) of the solution than that of a locally drawn very small volume sample. Also, the ability to do the original sampling in a larger volume size facilitates the engineering of the automated sampling and other processes such as filtering, so that macroscale devices such as sampling lines, pumps (e.g. syringe pumps), valves, filters, seals can be employed. Significantly, such subsampling can affords improved reliability and reproducibility of the size of the subsampled sub-aliquot, which can be important in providing a comparative basis. The subsampling approach also improves precision and sensitivity of analysis, since in preferred embodiments, it allows for on-line combination of sampling and analysis (i.e., direct fluid communication between the sampling unit and the analytical unit) without the need for further handling of subsampled sub-aliquot.

The sub-aliquot can be of any volume suitable for detection, but can generally be as small as less than about 100 µl, preferably less than about 50 µl, and in some cases, less than about 20 ul, less than about 10 ul, less than about 5 ul, or less than about 1 ul.

In a further preferred protocol that is related to the subsampling protocol described in the immediately-preceding paragraphs, the method can further comprise, after subsampling a sampled aliquot to obtain a sub-aliquot of the solution, the step of then returning a remainder portion of the sampled aliquot to the solution, the remainder portion being the portion of the orginally-sampled aliquot that was not included within the sub-aliquot obtained by subsampling. Advantageously, returning the remainder portion from each of the subsampled aliquots to the solution has the net effect of minimizing the amount of solution that is ultimately permanently taken from the solution. That is, the net depletion of solution is only the amount of the sub-aliquot obtained by sub-sampling. Another significant advantage of returning the remainder portion to the solution relates to a particularly-preferred embodiment in which the sampling path for the original sampling is physically the same as the remainder-return flow path, but with the fluid direction reversed relative to the forward, sampling flow path. In this embodiment, for example, an in-line filter can be used in the flow path allowing for filtering of the sampled aliquot during withdrawal of the aliquot in the sampling path (forward direction) on the way to a sub-sampling device, and after subsampling, the in-line filter can be backflushed by the remainder portion during return of the remainder portion in the remainder-return flow path (reverse direction). More details about filtering are described below. In this latter-described embodiment, the repetitive nature of the aspirating of samples and returning of remainder portions can be viewed as a repetitive pulsating of fluid (with repetitive alternating flow in the forward and reverse directions) through the same sampling flow path.

The above description details the methodologies by which the sampled aliquots are subsampled to obtain accurate, reproducible very small volume samples as sub-aliquots of the solution, and also to thereby result in the formation of a remainder portion of the sampled aliquots, and the methodologies by which the remainder portion of the sampled aliquots is returned to the solution. Such methodologies can be advantageously effected using the system described below in connection with the preferred embodiments of the invention.

In particular, such methodologies can be effected using, in a preferred embodiments, using an automated sampling probe for sampling a portion of the solution from the container at least twice during the dissolution period, and to obtain first and second aliquots of the solution. The sampling probe preferably has a distal end positionable in fluid communication with the solution in the sample container, and a proximate end that is in fluid communication with a sub-sub-sampling device that is configured for subsampling a portion of each of the sampled aliquots of the solution to obtain sub-aliquots of the solution. The automated sampling probe is preferably a component of an automated liquid handing unit or system comprising the sampling probe together with a robotic arm for translating the sampling probe for positioning, and a pump in fluid communication (e.g., selectable or continuous fluid communication) with the sampling probe. The pump provides a motive force at least for withdrawing a portion of the liquid sample into the probe to effect sampling (i.e., aspirating a sample). In some embodiments, the same pump or a different pump can provide a motive force for returning the remainder portion of the subsampled aliquots to the sample container. The pump can be a positive-displacement pump, such as reciprocating pump. In preferred embodiments, the pump is a syringe pump.

The sub-sampling device is preferably a sampling valve that provides fluid communication between the proximate end of the sampling probe and the pump. The sampling valve can be a multi-port sampling valve having at least one sample loop, with the volume of at least one of the sample loops corresponding to the size of the desired sub-aliquot of the sample. The sampling valve can be advantageously configured so that the following are acheived: in one selectable position, an aliquot of the solution is aspirated using the sampling probe and at least part of the sampled aliquot is loaded into the sample loop through a sampling flow path from the proximate end of sampling probe towards the first pump (e.g., in a forward direction); in another selectable position, a remainder portion of the subsampled aliquot is retuned to the container through a remainder-return flow path from the first pump towards the proximate end of the sampling probe (e.g., in a reverse direction), but which bypasses the sample loop; and in one selectable position (that can be the same as the earlier-noted positions or different from one or both thereof), the contents of the sample loop are discharged from the sampling valve as a sub-aliquot of the sampled aliquot (e.g., sent to an analyzing unit). The volume of the sample loop can be of any volume suitable for detection, but can generally be as small as less than about 100 μl, preferably less than about 50 μl, and in some cases, less than about 20 ul, less than about 10 ul, less than about 5 ul, or less than about 1 ul.

The operation of the sampling probe, and the operation of the sub-sampling device (e.g., multi-port sampling valve) are preferably controlled by a microprocessor under automation software.

Make-Up of Liquid Media (Feature G)

The method can further comprise providing make-up aliquots of a liquid media to the solution, with each of the make-up aliquots having a volume about the same as the volume of the sub-aliquots that are obtained from subsampling of the sampled aliquots withdrawn from the container. In this manner, particularly when used in connection with returning the remainder portion of the subsampled aliquots to container, the overall volume of the dissolving sample in the container can be maintained to be substantially the same over time. This makes the determination of concentration to be more directly comparable between samples, without having to adjust for a change in concentration due to depletion of overall volume of the liquid in the dissolution container. Hence, in a preferred protocol, a first make-up aliquot is provided to the container after sampling to obtain the first aliquot of the solution, and before sampling to obtain the second aliquot of the solution. The solution is then sampled again to obtain the second aliquot, the second aliquot is subsampled to obtain the second sub-aliquot, the remainder portion is optionally returned, and a second make-up aliquot is provided to the container, preferably before a third or subsequent aliquot is withdrawn from the sample container.

The liquid media used as the make-up volume can be the same as the solvent into which the sample material was dissolved. As noted below, however, the make-up liquid media can be different in chemical composition than the original solvent, such that repetitive addition of make-up aliquots can result in a time-varying change in the solvent to which the sample material is exposed during the dissolution period. For example, each make-up aliquot can add an additional amount of an agent that changes a property of the dissolution solvent environment, such as pH, ionic strength, etc.

The above description details the methodologies by which a make-up volume, preferably corresponding to the very small volume taken as sub-aliquots of the solution, can be added to the container during the dissolution period. Such methodologies can be advantageously effected using the system described below in connection with the preferred embodiments of the invention.

In particular, such methodologies can be effected using for example, a dispensing probe (e.g.,such as the dispensing probes described above in connection with initiation of dissolution) to provide the make-up volume directly to the container. In an alternative or supplemental embodiment, such make-up volumes can be provided using the automated sampling probe, in combination with the multi-port sampling valve as described above. For example, the sampling valve can be configured in a selectable position for loading a make-up liquid media into a sample loop, and in another selectable position, for providing the make-up liquid media to the container, for example, through a flow-path that is the same as the remainder-return flow path from the sampling valve to the proximate end of the sampling probe, but which is aligned through the sampling valve to a different source reservoir of make-up liquid media and a different pump. The sample loop for the make-up liquid media can be the same as the sample loop for subsampling to obtain the sub-aliquot of the solution. Further details and variations in such systems are described below.

Agitation (Feature H)

As noted, the dissolution profiling methods and systems of the present invention will be particularly advantageous in connection with dispersions comprising a solid sample material that is partially dissolved in a solvent to form a solution, and that is partially undissolved and dispersed in the solution. Such dispersions (or suspensions) can be agitated or mixed. Such agitation or mixing can help ensure sufficient contact between the undissolved solid sample materials and the solution during the dissolution period, and can provide a physical averaging of the solutions with respect to the property of interest (e.g., concentration). Such agitation or mixing can also help maintain the dispersion, preferably as a substantially uniform dispersion. Preferably, the dispersion is sufficiently uniform that it is free of continuous stratification layers that would be of a thickness that reflects in a change in a bulk property (e.g. optical turbidity, density) of one layer versus another layer.

The particular type or nature of agitation or mixing is not critical to the invention. For example, the contents of the container can be agitated or mixed by stirring, shaking, rocking, etc. Orbital shakers, magnetic stirring, shaft-driven stirring, etc. can be employed to effect the agitation or mixing. In particular, such agitation or mixing can be advantageously effected using the system described below in connection with the preferred embodiments of the invention.

Filtering (Feature I)

As noted above, each of the sampled aliquots of the solution can be filtered during or after sampling to obtain filtered sampled aliquots of the solution. Preferably, such filtering is effected during or after sampling, but prior to subsampling. Filtering is particularly advantageous with respect to applications for evalutating the dissolution profile of a sample material in a dispersion, so that undissolved sample materials can be retained in the solution rather than included in the sampled aliquot. This is particularly significant for evaluations done with relatively small amounts of sample material (e.g., less than 10 mg as described above), since removing undissolved sample materials from such dispersions can have affect the dissolution rate being determined.

The above described filtration methodologies by which sampled aliquots are filtered can be advantageously effected using filtering systems known in the art. In preferred approaches, the filtering can be effected using the system described below in connection with the preferred embodiments of the invention.

In particular, such filtering can be effected using for example, an in-line filter that is integral with or in fluid communication with the proximate end of an automated sampling probe, where as above, the sampling probe has a distal end and a proximate end, the distal end of the sampling probe being positionable in fluid communication with the solution in the sample container for sampling a portion of the solution to obtain sampled aliquots. Hence, the filter can be in-line in the sampling flowpath between the container and the sub-sampling device. In preferred protocols, the remainder portion of the subsampled aliquots are returned from the sub-sampling device to the solution through the same flow path as the sampling flowpath, but in the reverse direction, such that the remainder portions of the sub-aliquots back-flush the in-line filter while being returned to the solution in the reverse flow direction. Such "pulsating" action can be rapidly effected using the apparatus and method disclosed below in connection with the preferred embodiment.

Sampling Frequency/Sampling Plan (Features J, K)

Subsequent aliquots of the solution are preferably sampled with a relatively fast sampling frequency, where the sampling frequency is defined by the difference in time between sampling of successive aliquots (e.g., the difference between the first time and the later second time at which the first aliquot and the second aliquot are sampled, respectively). In preferred protocols, the sampling frequency is not more than about 2 minutes, and more preferably not more than about 1 minute. For many applications, including for example for investigations into drug candidates or drug compositions, the sampling frequency for at least two successive samples, and preferably for at least three successive samples, can be even faster, including for example not more than about 1 minute, preferably not more than about 40 seconds, or in some cases not more than about 30 seconds, not more than about 20 seconds or not more than about 10 seconds.

It will be appreciated by a person of skill in the art that the sampling frequency can depend on the nature and throughput of the analytical protocol and analytical unit being used (e.g., for determining the concentration of the sample material in the solution). Generally for applications involving analytical protocols/units involving separation of the subsampled subaliquot into one or more components (e.g., via one or more HPLC columns), the sampling frequency will preferably range from about 30 seconds to about 2 minutes, and preferably from about 30 seconds to about 1 minute. For applications that are not involving separation of the subsampled subaliquot into one or more components (e.g., via flow-injection analysis), the sampling frequency can be higher, including for example, ranging from about 10 seconds to about 2 minutes, and preferably from about 10 seconds to about 1 minute or from about 10 seconds to about 40 seconds or from about 10 seconds to about 30 seconds.

In particularly preferred embodiments, the protocols of the invention can include a sampling plan for efficient sampling, particularly for efficiently sampling multiple members of an array of sample materials. In one embodiment, for example, a sampling plan includes for each sample, sampling the solution at least six times, and preferably over at least two distinct sampling intervals. A first sampling interval comprises at least three sampled aliquots at three successive times and is, as described above (in connection with Feature D), preferably proximate in time with the initiation of dissolution, so that an initial part of a dissolution profile can be obtained for a sample material. A later-in-time second sampling interval also preferably comprises at least three sampled aliquots at three successive times. The sampling frequency within the first sampling interval, and within the second sampling interval is preferably less than about 1 minute, and even faster as described above (in connection with Feature J). The non-sampling interval that defines the time period between the end of the first sampling interval and the beginning of the second sampling interval is preferably at least not less than two times the greatest sampling frequency used in connection with any adjoining sampling interval, and more preferably three or four or five or six or seven or eight or nine or tent times such sampling frequency. In some applications, including for example for evaluating dissolution of drug candidates or drug compositions, the non-sampling interval can be at least sufficient to allow for the asymptotic maximum solubility to be approached for each solution system being evaluated (e.g., for that amount of solute in that amount of solvent at that temperature(s)). This sampling plan is advantageous in that it obtains data from an early part of the dissolution, substantially proximate in time with the initiation of dissolution, and then obtains data from a much later part of the dissolution, where the time-rate-of-change of the concentration of the sample material is much lower than at the early part of the dissolution, and therefore, with as few as six sampled aliquots, can establish a substantial portion of the dissolution profile. The advantage of such sampling efficiency is particularly noted with regard to evaluating small amounts of sample materials.

A further advantage of such a sampling plan is that it allows for interleaved sampling protocols that can be advantageously applied in connection with the evaluation of multiple members of an array of sample materials. For example, in an array comprising four or more multiple sample materials, each of the sample materials could be sampled with respect to the first sampling interval (as described above), with then the second sampling interval (as described above) being initiated after the first sampling interval is completed for each of the four or more sample materials.

In another embodiment of a sampling plan for efficient sampling, particularly for efficiently sampling multiple members of an array of sample materials, one may be less interested in sampling immediately after initiation, but rather, sampling more frequently after an induction period (e.g., allowing time-delayed disintegrants to take effect). In such a case, there may again be only a single sampling interval (temporally sequenced near the inflection point of the solubilization curve or dissolution profile), or two or more sampling intervals or three or more sampling intervals. Such a plan can include, for example, a first sampling interval comprising at least one sampled aliquot to establish a baseline point, preferably proximate in time with the initiation of dissolution, and a later-in-time second sampling interval preferably comprising at least two, more preferably at least three sampled aliquots at three successive times to establish the inflection point or other point at which the maximum time-rate-in-change of determined concentration exists. The jplan may further include a later-in-time third sampling interval preferably comprising at least one sampled aliquot to establish an asymptotic maximum value (e.g. solubility) to be approached for each solution system being evaluated (e.g., for that amount of solute in that amount of solvent at that temperature(s)).

Dissolution Environment

The dissolution environment—including for example, the composition of the solution in which dissolution occurs during the dissolution period, and/or the temperature or other properties during the dissolution period, and/or the temperature and/or humidity and/or other environments to which a sample material is exposed prior to the dissolution period—can be controlled, including as a parameter of the evaluation. Temperature is a particularly preferred parameter to control during a dissolution period, since solubility and solubilization rate can vary as a function of temperature. For example, the protocols (including the methods and systems) of the invention can be adapted to control the temperature of the solution at a desired temperature or within a desired range of temperatures, typically defined by upper and lower setpoints of a temperature controller. In some applications, for instance, one can control the temperature to be at or near or including ambient or room temperature (e.g., about 25 deg. C.) or at or near or including normal body temperature (e.g., about 37 deg. C.). If an array comprising multiple sample materials as members are being evaluated, for example while residing on a common substrate, the array (e.g., the substrate) can be controlled individually, as subgroups or groups, or as an array as a whole. For example, the array can be enclosed in an environmental controlled chamber so that the atmospheric environment (e.g., temperature, humidity, and the like) of the members of the array can be controlled. Environmental control, including temperature and/or humidity controlled chambers, is described in Ser. No. 60/451,463 entitled "Novel Methods and Apparatus for Evaluating the Effects of Various Conditions on Drug Compositions Over Time" filed Mar. 1, 2003 by Carlson et al.

Dynamic Dissolution Environment (Feature L)

The dissolution environment—such as especially the composition of the solution in which dissolution occurs during the dissolution period, and/or the temperature or other properties during the dissolution period—can be maintained to be substantially the same, or can be varied, and preferably controllably varied over time during the dissolution period. Advantageously, such capabilities can be used to obtain a dissolution profile that is representative of dissolution in a dynamic environment. In one non-limiting example, it may be desirable to mimic the environment along various regions of the gastrointestinal tract. For example, the pH of dissolution solution intended to mimic the gastrointestinal tract may be controllably varied from about neutral or slightly basic (e.g., representing the mouth at pH of about 7 or slightly higher), to more acidic (e.g., representing the stomach at pH ranging from about 2 to 4), to more basic (e.g., representing the intestines at pH ranging from about 7 to 9). Other properties that can be varied, and preferably controllably varied include temperature, ionic strength, ratio of solvent to co-solvent, solubilizer concentration, disintegrant concentration, surfactant concentration, wetting agents, etc.

Such variation can be effected by adding a liquid-media as a make-up agent, as described above, where the liquid-media is effective for changing one or more of said solution properties over time. Alternatively or supplementally, solid or liquid agents or co-solvents can be added directly to the solutions, for example using a dispensing probe as described above.

Analysis

The sampled aliquots of the solution (or in preferred embodiments, the subsampled sub-aliquots of the solution), are analyzed to determine the concentration of the sample material in the aliquots. The determined concentration of each of the successively-sampled aliquots, when considered in combination with the corresponding times at which the solution was sampled to obtain the aliquots, represents a dissolution profile for the sample material being dissolved. Where the surface area of the sample material is known or determined, the methods can further comprising determining an intrinsic dissolution rate for the sample material for one or more times during the dissolution period. Alternatively, where the surface area of the sample material is not known, or where a screening application (comparative evaluation between two or more sample materials) is desired, such as in combinatorial applications involving an array comprising multiple sample materials, the method can further comprise comparing the relative dissolution rates for the sample materials being evaluated for one or more times during the dissolution period.

The particular manner of analysis is not narrowly critical to the invention. Analysis can be effected, for example, using techniques known in the art. Generally, the analysis methods can be classified as those involving separation of one or more components of a sampled aliquot or sub-aliquot from other components thereof, and those that do not involve such separation. The analysis methods can also be classified as those adaptable for use in connection with a to-be-analyzed aliquot in a flow mode (e.g., analyzers having flow detectors of capable of analyzing samples coming from a flow system).

Analysis can be effected using an analytical system, such as the analytical system described below in connection with the preferred embodiments of the invention. In particular, such analysis can be effected using for example, an analytical unit comprising a detector, and in some cases a flow detector, each of which are in fluid communication with the sub-sampling device (e.g., sampling valve). The detector is adapted for detecting a property of the one or more separated components. The detector can be selected from one or more of a light-scattering detector (e.g., especially a static light-scattering detector, a dynamic light-scattering detector and/or a evaporative light-scattering detector ("ELSD"), a refractive index detector, a fluorescence detector, an infrared detector, and a spectroscopic detector (e.g., especially a ultra-violet/visible ("UV/VIS") absorbance detector. The analytical unit can further comprise a separation device in fluid communication with the sub-sampling device. The separation device can be adapted for separating one or more components of the subsampled sub-aliquots discharged from the sampling valve from other components thereof. Specifically, the separation device can be a liquid chromatography column.

Preferred analytical units can include a separation unit. The separation unit of the analytical unit be any device that can effectively separate components of the sub-sampled aliquot of the solution, including for example, separation units such as high performance liquid chromatography (HPLC), liquid chromatography (LC), gel permeation chromatography (GPC), gas chromatorgraphy (GC), capillary electrophoresis (CE), capillary electrochromatography (CEC), and the like. Thin-layer chromatography (TLC) can also be employed. Especially preferred analytical units include a liquid chromatography unit or a flow-injection analysis unit. The flow-injection analysis unit can be a continuous flow, stop-flow or variable flow system.

Combinatorial Research with High-Throughput Dissolution (Feature M)

The aforementioned protocols (including specific methods and/or devices) can be applied to a high-throughput method and system for evaluating a library or an array of sample materials. An array is an association of two or more, preferably four or more, most preferably eight or more members, such as sample materials. The array can comprise multiple members of sample materials in containers formed on or supported by a common substrate.

The aforementioned protocols can be effected in connection with each of the plurality of members of the array, generally either sequentially in time (i.e., serially), or simultaneously in time (i.e., in parallel). Also, it is possible that some steps of the methods are effected serially (e.g., sampling of aliquots), while other steps of the methods are effected in parallel (e.g., analysis), in each case as compared between different members of the array. The members of the array can be varied from each other in a number of ways, including for example differing with respect to chemical composition, differing with respect to crystalline structure (polymorphs), etc. In some embodiments, the material samples that are members of an array will be chemically and physically substantially the same (e.g., have the same chemical composition and same crystalline structure), and the method will comprise creating a different dissolution environment (e.g., different solvents, different temperatures, different ratios of cosolvents, different concentrations of additives) for each of the members of the array.

The array of library members for dissolution screening can be advantageously prepared using high-throughput formulation methods and systems. These can be accomplished for example, by using a formulation station such as that described by art disclosed methods and apparatus including, without limitations, the methods and apparatus described in detail in the PCT Publication No. WO 03/014732, and in U.S. Ser. Nos. 10/156,222, 10/156,245, 10/156,329, now abandoned, and 10/156,295 and in the commonly owned and co-pending PCT Publication Nos. WO 00/23921; WO 02/31477 A2, and WO 02/14391 A2, which are hereby incorporated by reference in their entirety. See also PCT Publication No. WO 99/52962 and U.S. Ser. No. 09/640,094 entitled "Procedure And Device To Develop Nanodispersants" filed Aug. 17, 2000 by Sebrof et al., which is hereby incorporated by reference.

For example, formulation by wet and/or dry milling can be used. Such formulation is comprised of dispensing with an art disclosed liquid handling robot all components such as drug candidate, excipients, stablilizers, surfactants, and the like into an array of vials. If a solvent is used to dispense the components, it can be stripped off either by vacuum or by blowing dry nitrogen directly on the array. Milling media is then added to the array by means of solids dispensing. The milling media can be any art-disclosed milling media such as glass beads of various sizes (e.g., 0.5 mm to 6 mm), stainless steel beads of various sizes (e.g., 0.5 mm to 6 mm), polymer beads (e.g., PS-DVB beads) of various sizes (e.g., 50 um-1 mm), and combination thereof. Wet milling is accomplished by adding an art-disclosed suitable aqueous media along with appropriate art-disclosed wetting agents. Milling is preferably done in parallel with the use of a 5 g Harbil mixer but other suitable art-disclosed mixers may also be used. Various degrees of mixing can be achieved by using various combinations of mixing media and various mixing times. After the mixing is completed, the formulation is separated from the milling media preferably by centrifugation and/or filtration.

The formulation process can be controlled by computer to automatically mix specific quantities of material (e.g., drug candidates, solvents, stabilizers, etc.) to form a material composition. The materials may be mixed in accordance with library designs produced by computer—preferably with library design software such as Library Studio® (Symyx Technologies, Inc., Santa Clara Calif.). Automatic control of the formulation station 1130 enables the present invention to prepare several libraries or members. Moreover, automated control reduces possible errors that can be caused by manual control. In addition, automated control may enable the present invention to prepare relatively small sample sizes (e.g., ranging between nanoliter to milliliter sizes). This advantageously provides high throughput preparation and screening of the material compositions.

After the array of multiple sample materials are prepared, they may be screened by the dissolution methods disclosed herein. Specfically, a high throughput drug solubilization characterization or screening method and system is provided to identify, select, synthesize, and the form of a drug candidate having desirable dissolution properties. This solubilization screening method generally comprises: (1) providing a library comprising a plurality of members (i.e., sample materials), wherein each said library member comprises a drug candidate; (2) determining a dissolution profile for each of the plurality of library members for solubilization characteristics using any of the methods detailed in this application for determining a dissolution profile; and (3) comparing the dissolution for each of the plurality of library members. The solubilization screening system generally comprises: (1) a plurality of sample containers, preferably four or more sample containers, each for containing one member of the library or array for evaluation—either separately or structurally integrated (e.g, being formed in or supported on a common substrate); (2) one or more automated sampling probe; (3) an analytical unit that is either a serial/single-channel unit—adapted to analyze one sample material at a time, and a plurality of sample materials sequentially, or a parallel/multi-channel unit—adapted to analyze two or more samples simultaneously. Preferably such system also includes (4) one or more automated dispensing probes. In one parallel embodiment, the solubilization screening system comprises two or more sets of structurally integrated or structurally independent automated probes, each set comprising an automated sampling probe and an automated dispensing probe (e.g., each set being structurally integrated through a common probe head).

Such high-throughput solubilization screening can be applied alone or in combination with various other screening methods for evaluating other properties of interest, such as stability, compatability, solubility, crystallinity, particle size, etc. Taken in combination as part of a larger workflow, such screens can systematically enhance the efficiency of the process of drug development.

In preferred embodiments, all of the above-described steps of the high-throughput solubilization screening methods are automated and controlled by a computer. The formulation of libraries can also be automated and controlled by a computer. Preferred automation software is Impressionist® (Symyx Technologies, Inc., Santa Clara Calif.). User interfaces can enable users to input commands to computer via an input device—including any suitable device such as, for example, a conventional keyboard, a wireless keyboard, a mouse, a touch pad, a trackball, a voice activated console, or any combination of such devices. Input device enables a user to enter commands to perform drug selection, library building, screening, etc. If desired, input device may also enable a user to control the various workstations (e.g., for formulation or for solubilization screening). A user may also monitor processes operating on the systems on a display device, such as a computer monitor, a television, a flat panel display, a liquid crystal display, a cathode-ray tube (CRT), or any other suitable display device. Communication paths can be provided and configured to enable data transfer among the computer, the formulation workstation, the solubilization screening workstation, and user interfaces.

Preferred Embodiment for High-Throughput Dissolution Screening

Referring now to FIG. 1, the system 100 of the present invention is generally comprised of an automated dispensing unit 14, an automated sampling unit 20 and an analytical unit 34.

The automated dispensing unit 14 uses an automated dispensing probe 15 to dispense a first liquid 16 (e.g., a solvent) into a container formed as a well 11 of a substrate 10, where an amount of at least one sample material 12 is located. As shown, the automated dispenser is a an automated liquid dispenser that also comprises a pump 17 as a motive force for moving the liquid, and a probe head 19 configured with a robotic arm (not shown) and/or translation station (not shown) for positioning the probe head 19, and thereby a distal end of the dispensing probe 15 into or over the container, shown here as well 11. Dispensing of the first liquid (e.g. solvent) 16 into a well 11 that already contains the sample material 12 initates dissolution of the sample material into the solvent, to form the solution 18. Preferred liquid handling robots that can be used as the dispensing unit 14 include those sold by Tecan Systems (formerly Cavro Scientific Instruments) (San Jose, Calif.).

The automated sampling unit 20 shown in FIG. 1 comprises an automated sampling probe 21 for sampling a portion of the solution successively during the dissolution period. The sampling probe has a distal end 21a positionable in fluid communication with the solution in the sample container, and a proximate end 21b, and is generally shown as being supported by the probe head 19. The proximate end 21b of the sampling probe 21 is in fluid communication with a sub-sampling device 24, the sub-sampling device (e.g., sampling valve) is configured for subsampling a portion of each of sampled aliquots of the solution to obtain sub-aliquots thereof. The sampling unit 20 also includes an in-line filter (i.e., separation medium) 32 positioned in fluid communication with and in the flow between the sampling probe 21 and the sub-sampling device 24. Positioning of the sampling probe 21 is effected using the probe head 19 in combination with a robotic arm (not shown) or/or a translation station (not shown). A pump 22 (e.g., a syringe pump) is shown in selectable fluid communication with the proximate end 21b of the sampling probe 21 via sub-sampling device 24, for providing a motive force for withdrawing a portion of the solution into the probe 21 to effect sampling through a sampling flow path (in a forward direction), and in preferred embodiments, for returning remainder portions of the subsampled aliquots to the containers through a remainder-return flowpath (in a reverse direction) and/or for providing a make-up aliquot to the sample container through an make-up flow path (in the reverse direction). Although the pump 28 is shown as part of the analytical unit 34, this pump 28 can instead, or also be part of the sampling unit 20, in that context, can be considered as a second pump 28, for providing a make-up aliquot (i.e., replacement volume) of a second liquid media 30 into the solution 18 located in the container shown as well 11 on the substrate 10. The multi-functionality of pump 28 can depend, as is well known in the art, on the particular configuration of the sub-sampling device (e.g., sampling valve), some of which are described further below.

The analytical unit 34, as shown, comprises a detection device 27 that can include a detector 26, or multiple such detectors 26, that one or more of which can be a flow detector, but can also be a spatially-sensitive detector that operates in a non-flow mode (e.g. a region of pixels of a CCD camera). The analytical unit 34 can also comprise a mobile phase source reservoir 30 for containing a liquid media as a mobile phase (e.g., of a liquid chromatography system or of a flow-injection analysis system), and a pump 28 for providing a motive force for effecting flow of the mobile phase through the sub-sampling device 24 (e.g., sampling valve), to the detector 26.

Figure 2:
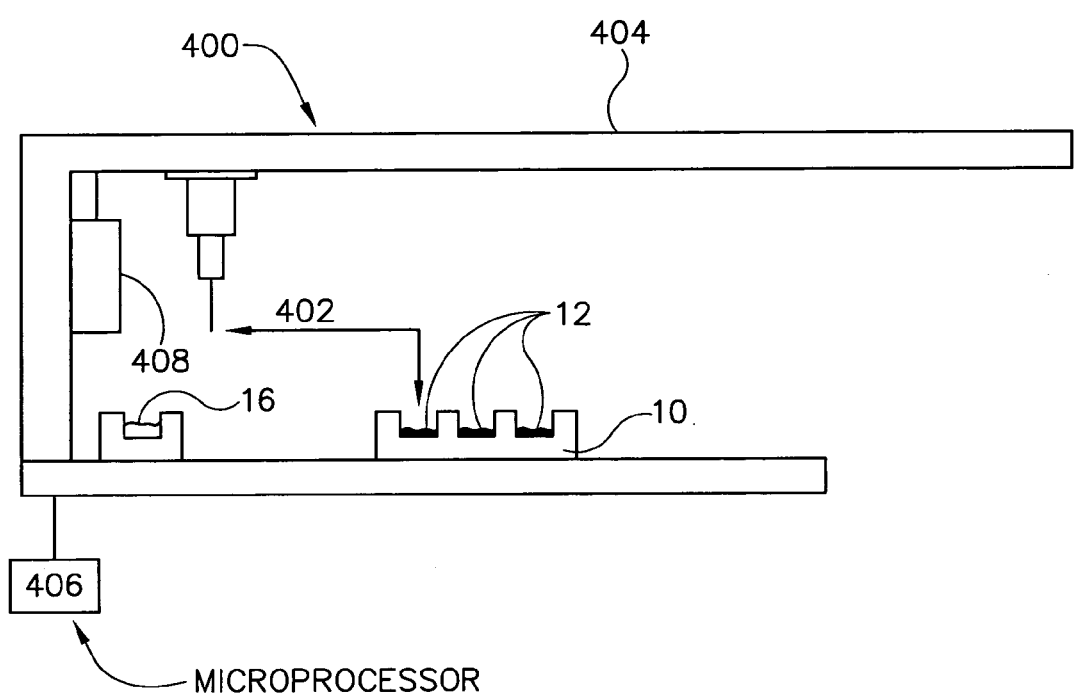
FIG. 2 shows a side view of a dispensing unit in accordance with the principles of the present invention.

Referring to FIG. 2, a preferred embodiment 400 of the dispensing unit 14 can comprise an injection probe or dispensing tip 402 mounted on a robot arm 404, a microprocessor 406 for controlling three-dimensional motion of the tip 402 between various spatial addresses, and a pump 408 for withdrawing the first liquid 16 into the tip 402 and dispensing the first liquid 16 onto the substrate 10 where the at least one sample 12 is located. The microprocessor 406 is preferably user-programmable to accommodate varying arrangements of the at least one sample 12 (e.g., square arrays with "n-rows" by "n-columns", rectangular arrays with "n-rows" by "m-columns", round arrays, triangular arrays with "r-" by "r-" by "r-" equilateral sides, triangular arrays with "r-base" by "s-" by "s-" isosceles sides, etc., where n, m, r, and s are integers). The tip 402 has a surface defining a cavity and a port for fluid communication between the cavity and the substrate 10. The tip 402 also comprises a port for fluid communication between a receptacle 10 for the first liquid 16 and line (not shown) and the cavity.

The dispensing unit 14 may further comprise a temperature-control element (not shown) in thermal communication with the tip 402 for maintaining the liquid 16 residing in the tip 402 at a predetermined temperature or within a predetermined range of temperatures. The temperature-control element can be, in the general case, a heating element or a cooling element (for low-temperature characterizations). The particular design of the heating element or cooling element is not critical. For example, the heating element can be a resistive-heating element such as a resistive wire in adjacent proximity to the sample cavity of the tip 402. The heating element can alternatively be a fluid-type heat-exchanger heating element having a fluid-containing tubular coil around the tip 402. In any case, the temperature-controlled tip 402 can have a body encasing the heating element, and preferably a thermocouple for temperature monitoring and control. In another alternative embodiment, the heating element can be the body of the tip 402 itself, where the body comprises a large thermal mass, preferably surrounded by an insulator. The large-thermal-mass body can be heated (or in the general case, cooled) by periodically allowing the body to thermally equilibrate with a hot environment such as a surface or fluid via conduction, convection or thermal radiation (or generally, with an cold environment). Advantageously, such a heated tip 402 can maintain the first liquid 16 at the required temperature while it resides in the cavity of the tip 402. As such, unlike conventional high-temperature characterization systems, the tip 402, as well as associated robotic arm 404, can be located external to (outside of) a heated environment (e.g., oven). Another example of a preferred dispensing unit 14 is further described in detail in commonly owned U.S. Pat. No. 6,175,409 B1, which is incorporated herein by reference in its entirety.

Figure 3:
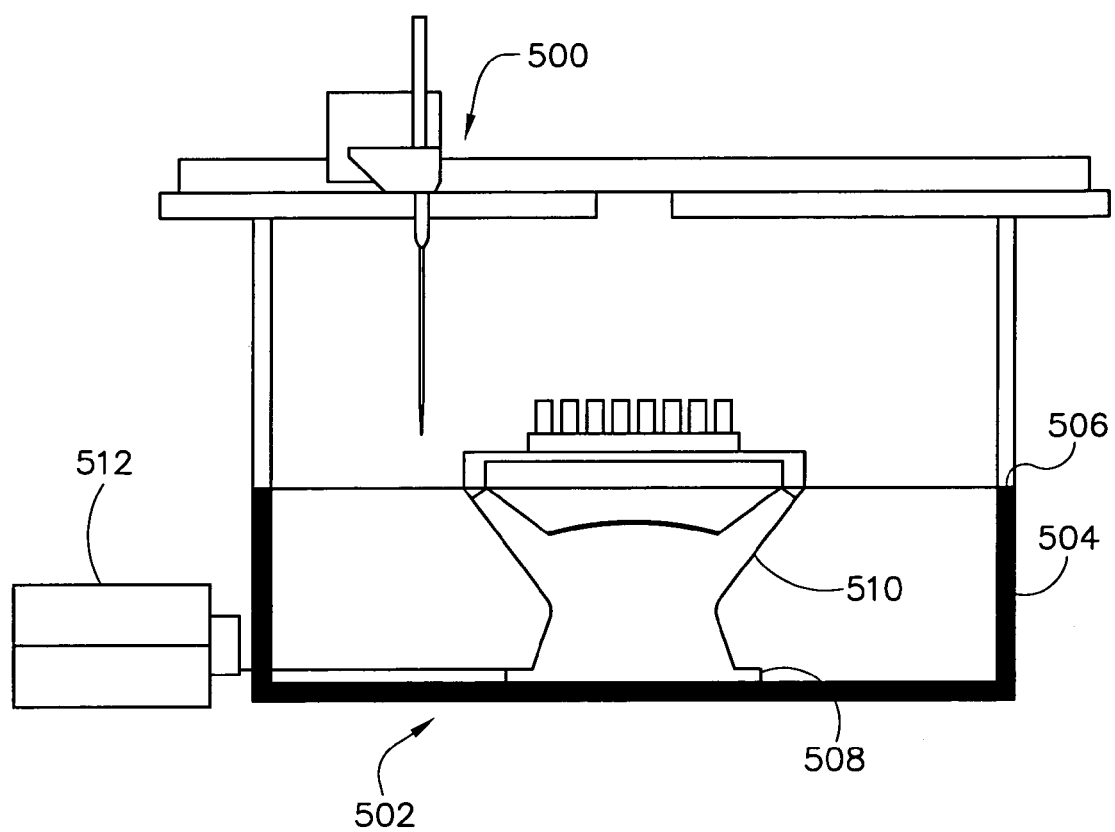
FIG. 3 shows a front view of a dispensing unit with a controlled agitation assembly in accordance with the principles of the present invention.

It is also preferred that a controlled agitation assembly 36 is included in the dispensing unit 14 to agitate the solution 18 during dispersion. The controlled agitation assembly can be any art disclosed device that provides agitation of the solution 18 such as magnetic stirrer, orbital shaker, parallel ball milling, rocker, sonicating probe, homogenizer, and the like. For example and referring to FIG. 3, a controlled agitation assembly 502 is included in the dispensing unit 500 having a resonant sealed enclosure 504 integrated into the dispensing unit's 14 base 506, and a voice coil motor 508 comprising of an audio subwoofer 510 (e.g., 1,500 W dual-coil audio subwoofer) and audio amplifiers 512 (e.g., two power amplifiers) providing a controlled variable frequency (e.g., 20 to 500 Hz) and amplitude (0–20 mm). In a preferred embodiment, the controlled agitation assembly is comprised of orbital shakers operating at a variable frequency, typically around 100 Hz, to provide vertical agitation of the solution 18.

Figure 4:
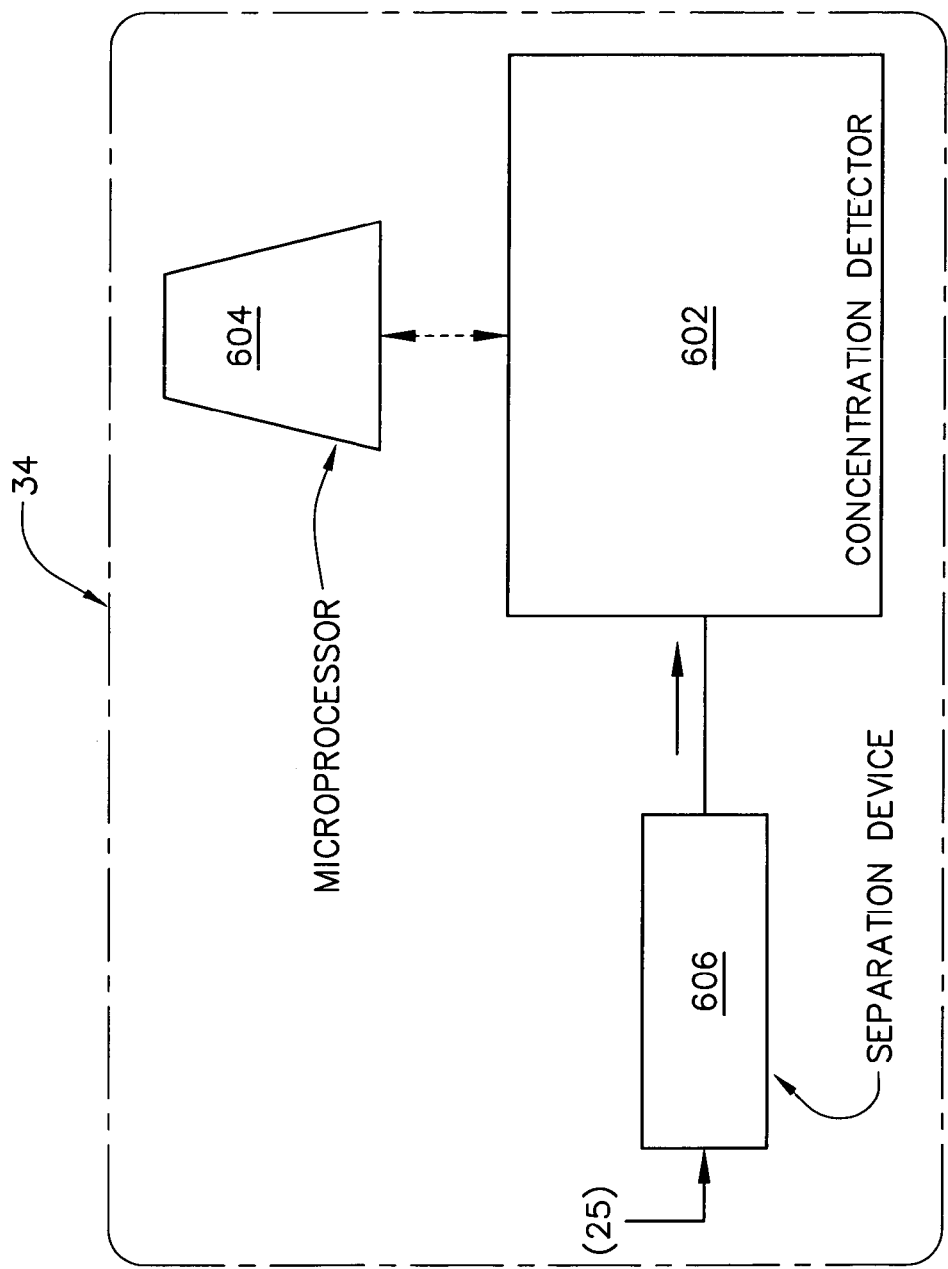
FIG. 4 shows a schematic of an illustrative analytical unit in accordance with the principles of the present invention.

Referring to FIG. 4, preferably also in connection with FIG. 1, the analytical unit 34 is used to determine the concentration of aliquots or subaliquots 25 drawn successively over time from a solution having a varying concentration of the sample material 12. The analytical unit 34 can be any art-disclosed device that is effective for determining concentration, such as shown in FIG. 4 as concentration detector 602—including such as an ultra-violet (UV) visual inspector, a refractive index detector, an infrared detector, an evaporative light scattering detector, a fluorescence detector, and the like. The concentration detector 602 is preferably a highly sensitive detector, being adapted for and with capability to detect concentration levels even in the range of about 0.0001 mg/ml to about 10 mg/ml.

Referring further to FIG. 4, in a preferred embodiment, the analytical unit 34 may further include a microprocessor 604 that records and translates the data obtained from concentration detector 602 into graphic and/or tabular numerical form (e.g., dissolution curve or dissolution profile) and can provide other information regarding solution 18. The same microprocessor 604 can also be used in connection with control of the automated dispensing unit 14 and/or the automated sampling unit 20. In a preferred embodiment, a separation device 606 is also included as a component of the analytical unit 34 and can be located upstream from the concentration detector 602. The separation device 606 (e.g., chromatography column) is used to separate and isolate one or more components of (e.g., various compounds contained in) the sampled aliquot or subsampled sub-aliquot 25 of solution 18, for detection by the concentration detector 602.

Since the separation process by the separation device 606 may in some cases require a longer time period than the time required for the sampling process by the sampling unit 20, it may be desirable to have parallel separation devices, with a single common injection valve. See, for example, U.S. Pat. No. 6,296,771, which is hereby incorporated by reference in connection with the apparatus and techniques disclosed therein. Alternatively, rapid-serial high-throughput techniques can be employed. See, for example, in connection with characterization of non-biological polymers, U.S. Pat. Nos. 6,406,632 and 6,461,515.

The sub-sampling device 24 is preferably a sampling valve, such as a multiport switching valve having at least one sample loop. The sampling valve or switching valve 24 can be constructed out of any suitable material such as metals, (e.g., stainless steel, aluminum, and the like), plastic, and ceramics. Materials such as aluminum or an aluminum alloy may be preferred because they have desirable thermal and structural properties.

Figure 5A:
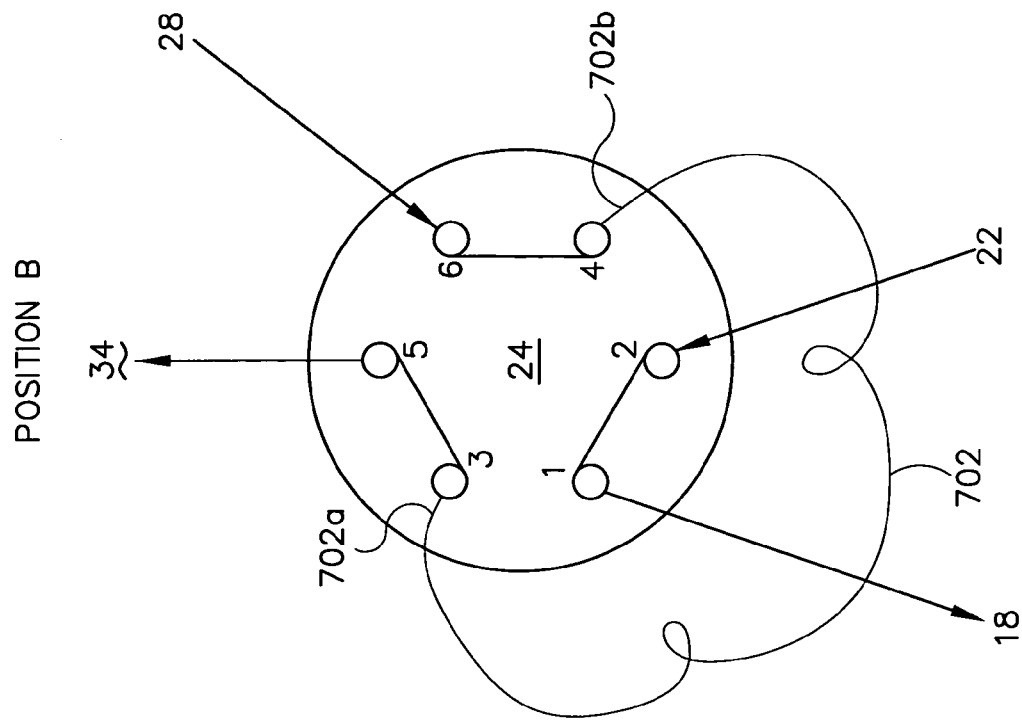
FIGS. 5A and 5B show schematics of illustrative multi-port sampling valves in accordance with principles of the present invention, including a six-port, single sample loop configuration (FIG. 5A) and a ten-port, two sample loop configuration (FIG. 5B)
Figure 5A:
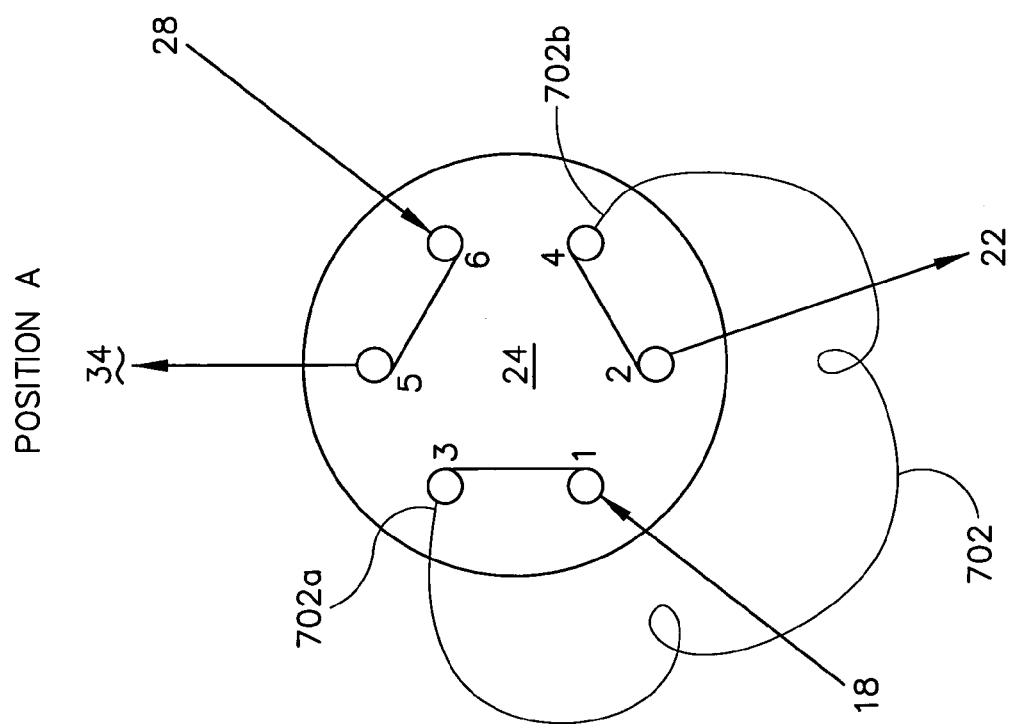

One configuration for the sampling valve 24 is shown in FIG. 5A. Briefly, as shown, sampling valve 24 is a multi-port sampling valve comprising a sample loop 702 and at least six ports (shown as being numbered 1–6), including a first port 1 in fluid communication with the proximate end (21b, FIG. 1) of the sampling probe (21, FIG. 1), and a second port 2 in fluid communication with a first pump 22, a third port 3 in fluid communication with a first end 702a of the sample loop 702, a forth port 4 in fluid communication with a second end 702b of the sample loop 702, a fifth port 5 in fluid communication with an analytical unit 34, and a sixth port 6 in fluid communication with a second pump 28.

The sampling valve 24 is configured so that in a first selectable position (shown as "Position A"), the first and third ports are in fluid communication with each other, and the fourth and second ports are in fluid communication with each other, for loading at least part of the sampled aliquot into the sample loop 702 through a sampling flow path from the solution 18 through the sampling probe (21, FIG. 1) towards the first pump 22. The sampling valve 24 is also configured so that in a second selectable position (shown as "Position B"), the sixth and fourth ports are in fluid communication with each other, and the third and fifth ports are in fluid communication with each other, for discharging the contents the sample loop 702 as a sub-aliquot of the sampled aliquot through a detection flow path from the second pump 28 to the detector 34. The sampling valve 24 is further configured so that in the second selectable position (shown as "Position B"), the second and first ports are in fluid communication with each other, for returning a remainder portion of the sampled aliquot not loaded into the sample loop 702 to the solution 18 in the container (e.g., well 11, FIG. 1) through a remainder-return flow path from the direction of the first pump 22 through the sampling probe (21, FIG. 1) to the solution 18.

Figure 5B:
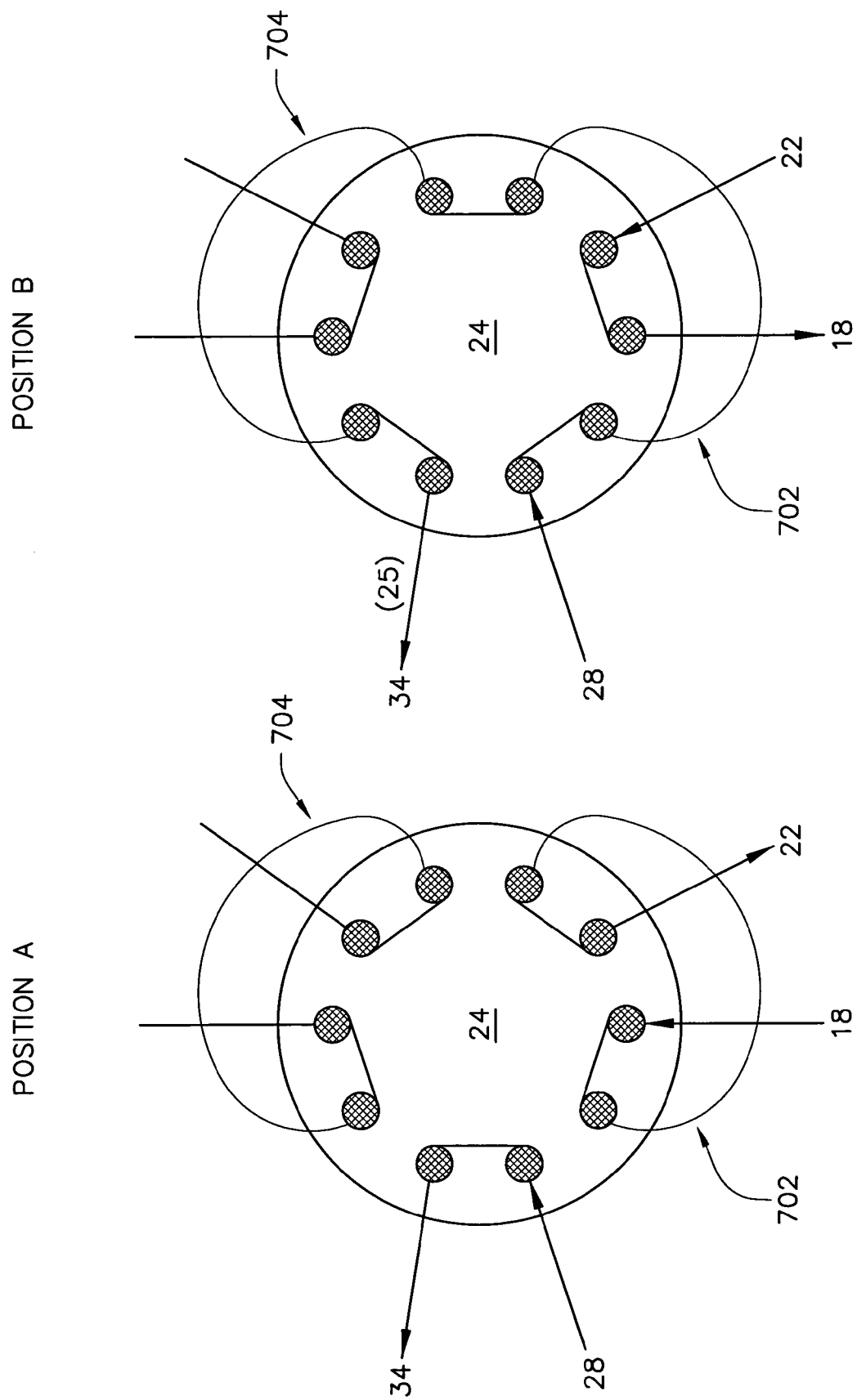

Referring now to FIG. 5B, another configuration is shown for the sampling valve. The sampling valve 24 as shown therein comprises first and second sample loops 702, 704 respectively, that can be used to subsample an aliquot to form a sub-aliquot for (optional separation) and for analysis by the analytical unit 34. While the sampling valve 24 is in one selectable position (e.g., position "A"), a first pump 22 aspirates a portion of the solution 18 contained in a well 11 formed in the substrate 10. The aspirated aliquot is drawn through filter 32 (FIG. 1), and a portion of the filtered sampled aliquot is then loaded into the sample loop 702. When the valve 24 is switched to a second selectable position (e.g., position "B"), the sub-aliquot loaded in the sample loop 702 is then discharged by the second pump 28 as sub-aliquot 25 to the analytical unit 34, the discharge path as shown in FIG. 5B including the detection flow path from the first sample loop 702, through the second sample loop 704 to the analytical unit 34. Meanwhile, with the sampling valve 24 in this position B, the first pump 22 returns the remainder portion of the filtered sampled aliquot to solution 18 in the container (well 11) through the sampling valve 24, but bypassing the sample loop 702. This process is repeated for each of the aliquots that is desired to be analyzed by the analytical unit 24. Note that sample loop 704 is functionally extraneous in this embodiment. Also, if a make-up aliquot is desired, it is not provided through the sampling valve 24 in this embodiment, but rather could be provided directly from an automated dispensing unit 14 (FIG. 1).

Figure 6:
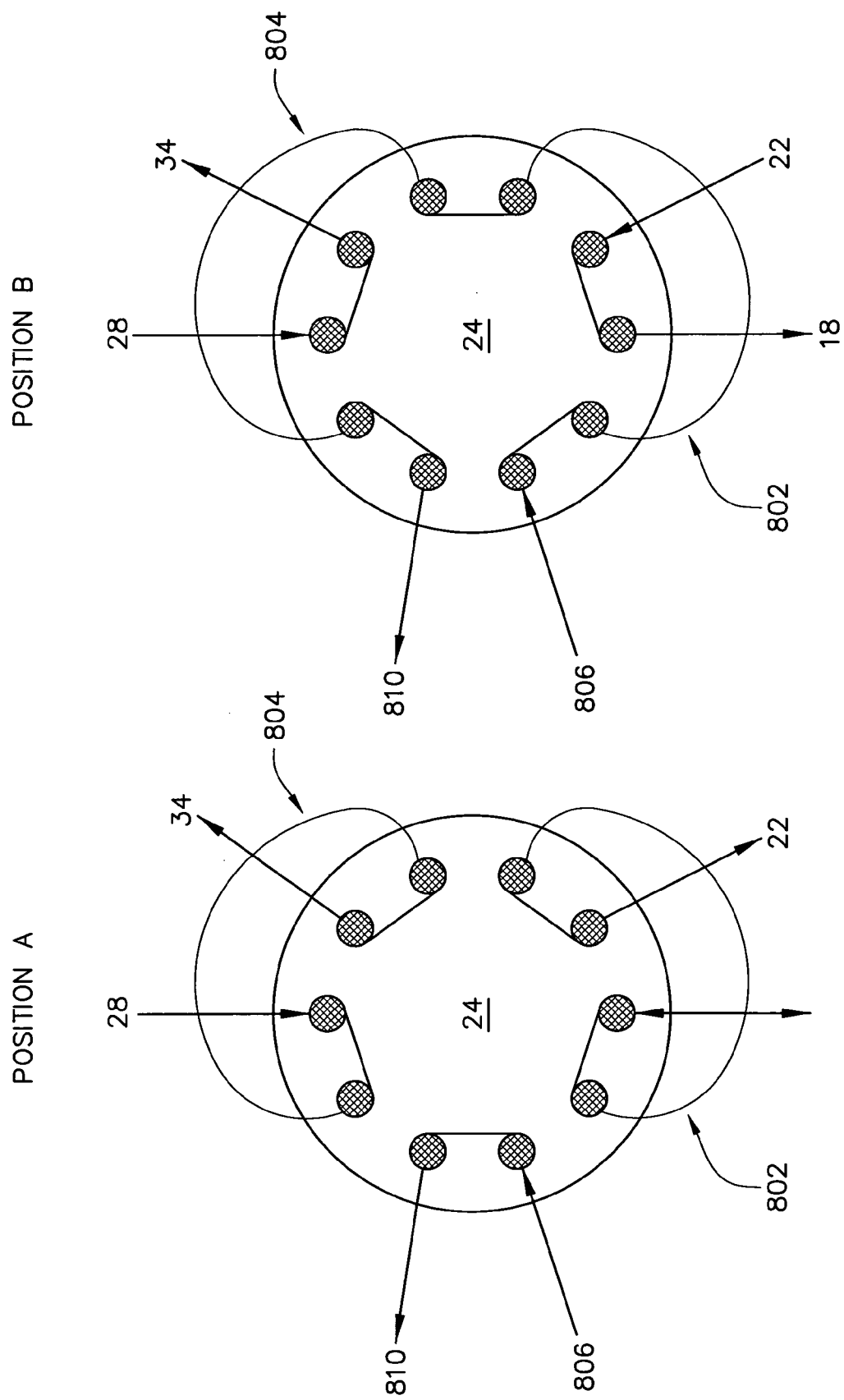
FIG. 6 shows a schematic of another illustrative multi-port sampling valve in accordance with principles of the present invention, including a ten-port, two sample loop configuration adapted to allow for providing a make-up aliquot of a liquid media to the solution being evaluated.

FIG. 6 provides another exemplary embodiment of a sampling valve 24, with multiple ports and two sampling valve. This sampling valve 24 affords the additional functionality of allowing for a make-up volume to be directly determined using the same sample loop as is used for sub-sampling to obtain sub-aliquot 25. While the valve 24 is in one selectable position (e.g., position "A"), the first pump 22 aspirates the solution 18 contained in well 11 formed in the substrate 10 through the valve 24, allowing a portion of the sampled aliquot to be loaded into the first sample loop 802. When the valve means is switched to a second selectable position (e.g., position "B"), a second pump 806 loads a make-up aliquot into the first sample loop 802, which in turn advances the sub-sampled sub-aliquot to a second sample loop 804. Meanwhile, the first pump 22 returns the remainder portion of the solution 18 back through the valve 24 into the sample container 11. Thereafter, the sampling valve 24 is switched back to the original position (e.g., position "A") at which point the pump 28 (which can be incorporated into or separate from the analytical unit 24) discharges the sub-aliquot 25 from the second sample loop 804 to the analytical unit 34. At the same time, the first pump 22 can provide the make-up aliquot from the first sample loop 802 back to the solution 18. This process is repeated for each of the sub-aliquots 25 that is desired to be evaluated by the analytical unit 24.

Although the above-described invention has been described for drug candidate compounds as the sample material, this invention may be practiced with any compound of interest as the sample material. Thus, the methods and systems described herein may be used for any element, compound or composition for which a determination of dissolution profile is desired.

The following examples provide illustrative examples on how the present invention can be used to perform the processes described above. These examples are for the purpose of illustration only and are not to be construed as limiting the scope of the invention in any way.

EXAMPLE 1

High Throughput Dissolution Screening of Aspirin

A 10 mg of powdered Aspirin standard from Aldrich was weighted into a 20 ml scintillation vial and put on a shaker at a robot platform. The shaker was then turned on and an automated dispensing unit with a 10 ml syringe dispensed 10 ml of deionized water into the 20 ml scintillation vial containing the 10 mg of Aspirin thereby initiating dissolution of the 10 mg of Aspirin into the 10 ml of deionized water to form, over time, a solution having an increasing concentration of aspirin.

Figure 7:
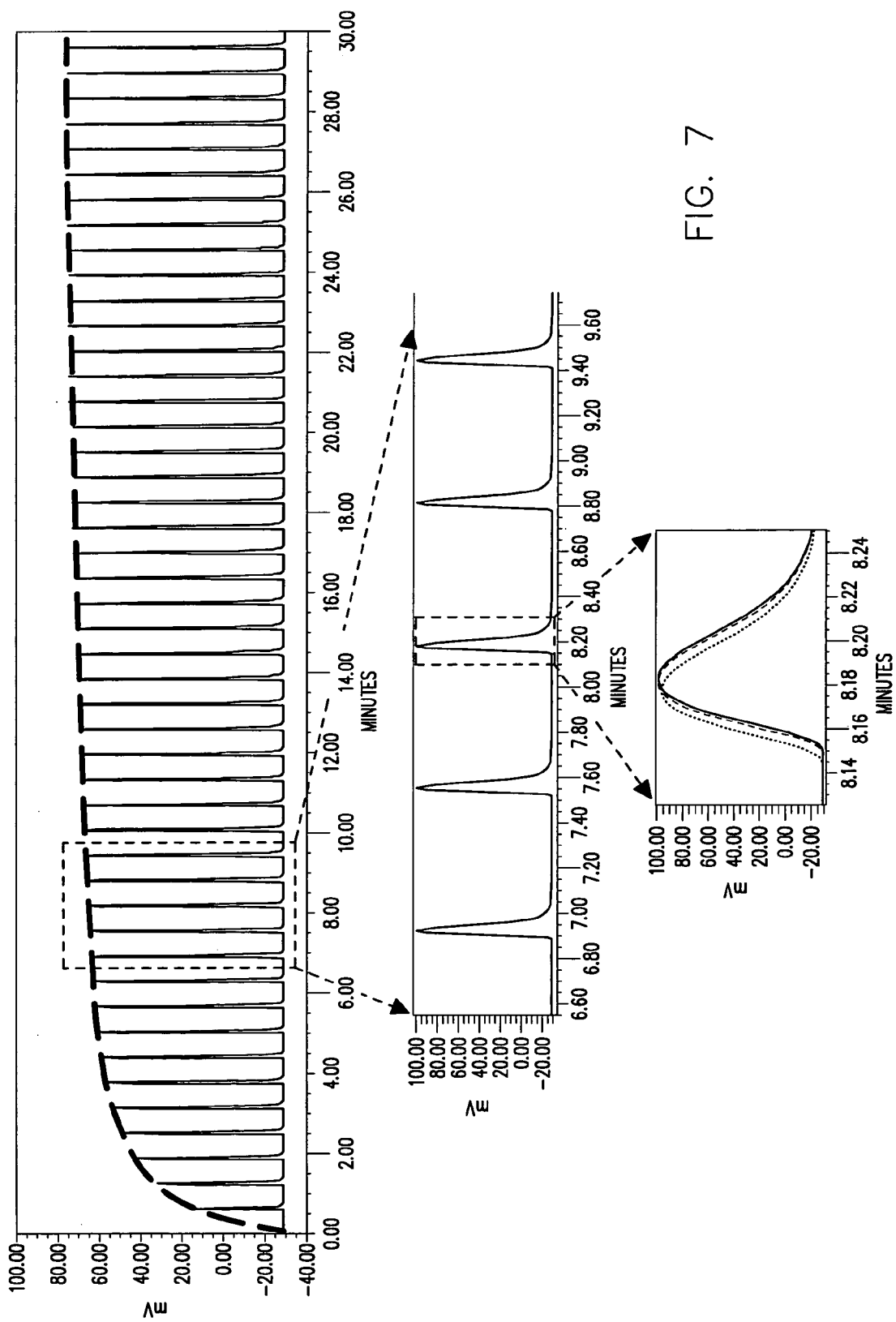
FIG. 7 shows a dissolution profile of Aspirin obtained from the protocols of Example 1.

Thereafter, an automated sampling unit aspirated approximately 300 uL of the solution (the sample itself never enters the syringe) through an in-line filter allowing a sampled aliquot of the filtered solution to enter a switching valve and fill a 20 uL sample loop connected to the ports of the switching valve. Once the 20 uL sample loop was filled with a portion of the aliquot, the switching valve was switched to a second position by automation, causing the sub-aliquot contained in the 20 uL sample loop to be discharged into an analytical unit. The analytical unit comprised a syringe pump and an UV detector, for determining concentration. At this point, the automated sampling unit returned the remainder portion of the filtered aliquot back through the filter and back into the solution contained in the scintillation vial. Such backflush thereby allowed the filter to be cleared and undissolved particles to be returned back into the container. Thereafter, the switching valve was switched back to its original position and this entire process was repeated with a 37 second sampling frequency between successive samples for 30 minutes total, yielding the dissolution profile shown in FIG. 7. FIG. 7 shows that the typical aliquot to aliquot variation in peak areas is approximately +/−5% and that the maximum dissolution of Aspirin was reached in less than 10 minutes.

EXAMPLE 2

High Throughput Enhanced Drug Solubilization of an Active Compound

Figure 8:
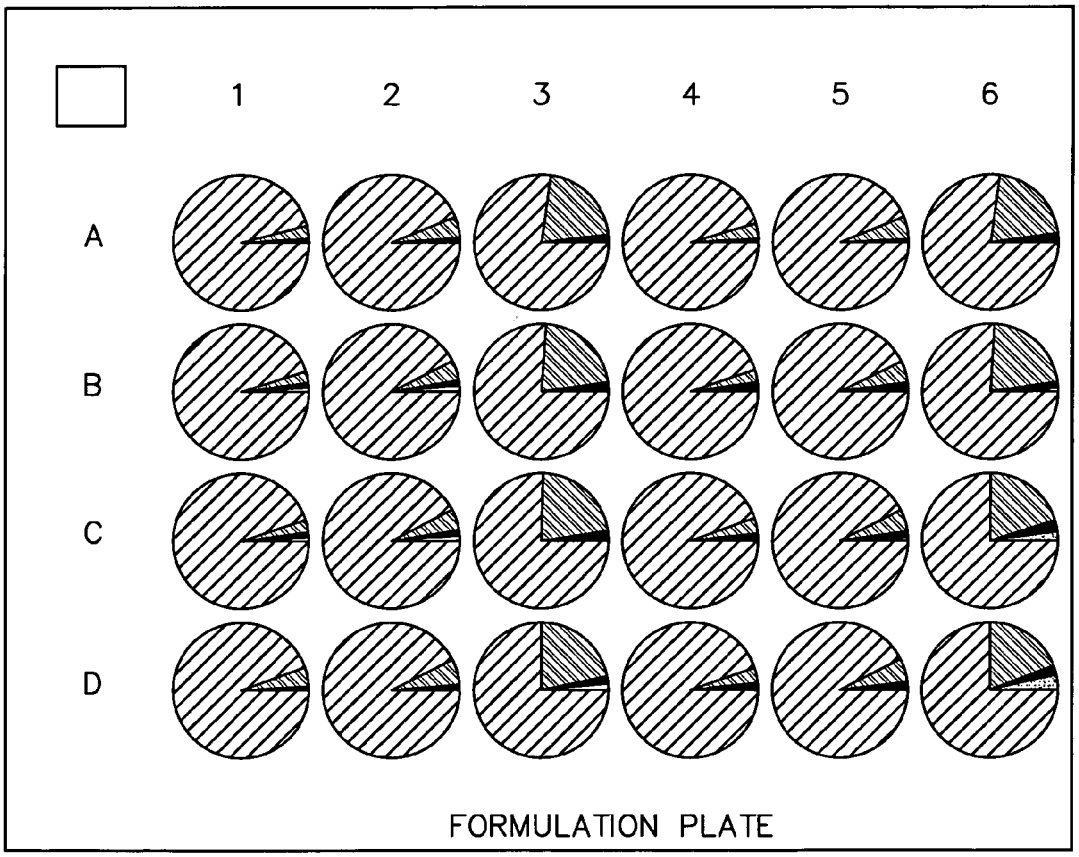
FIG. 8 shows a schematic of an illustrative library design of sample formulations used in Example 2.

A library of sample formulations of a poorly water-soluble active compound was prepared and screened using the methods and system of the invention. The library design for the experiment is shown in FIG. 8. Three concentrations of the active compound, four ratios of the active compound to stabilizer, and two stabilizers that differ in molecular weight were used as compositional variables, leading to a 24 well library. The volumes for the design were calculated by Library Studio® and saved to the computer database.

The formulation process was carried out by the formulation station comprising of a liquid handling robot equipped with Impressionist® software. (Symyx Technologies, Santa Clara, Calif.). The library design was read by the Impressionist® software, which then controlled the liquid handling robot to add the stabilizer to the appropriate wells by dispensing a concentrated aqueous solution of each of the stabilizers. The liquid handling robot subsequently topped off all wells to 800 uL. Agitation was turned on, and the liquid handling robot then added the appropriate amount of the volatile organic solution of the active compound to each well. The library of formulations was stirred for 4 hours to allow the volatile organic solvent to evaporate.

Figure 9:
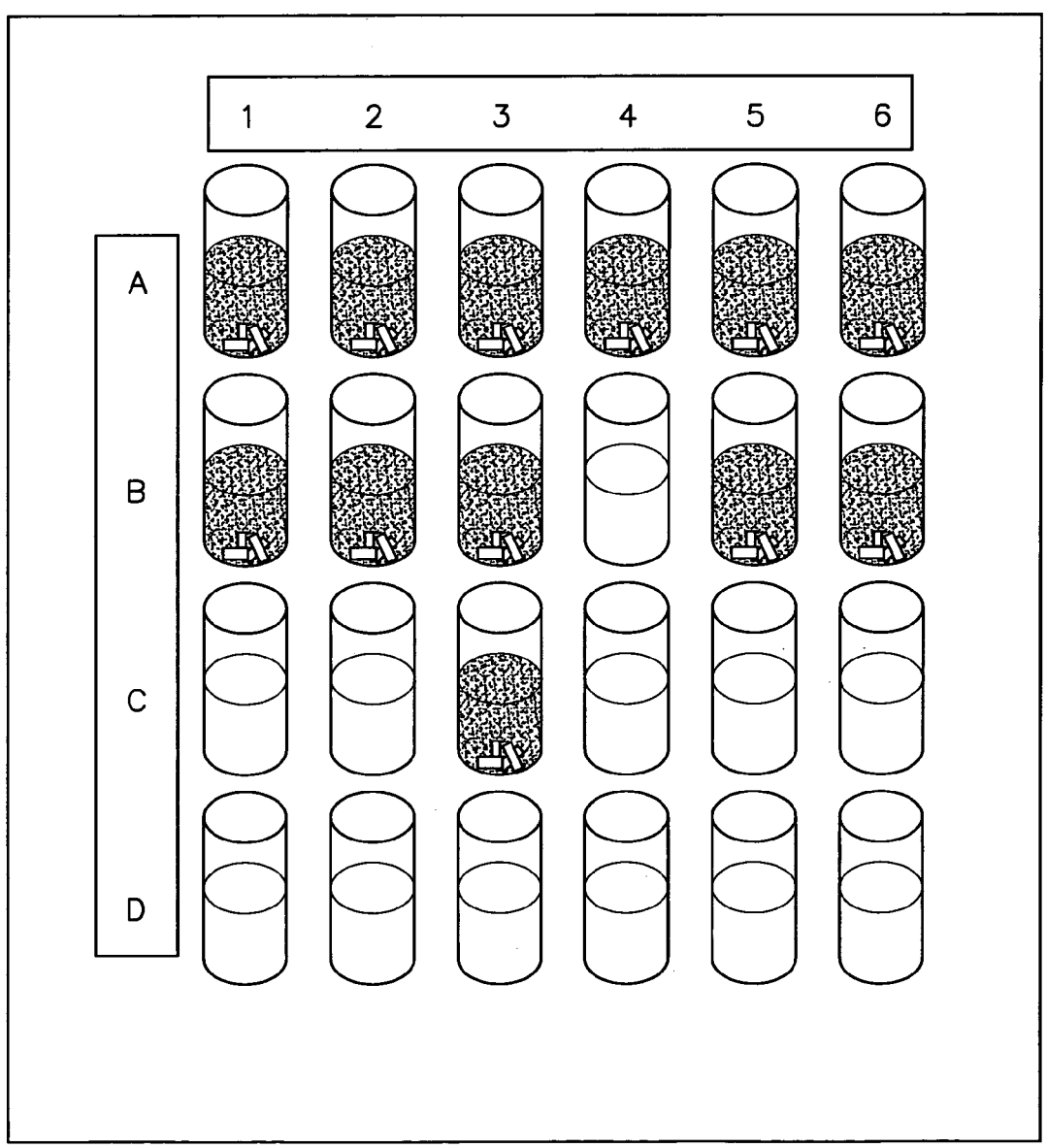
FIG. 9 shows a schematic of illustrative images of the library of sample formulations that could be obtained from a visual inspection screening used in Example 2.

Thereafter, each liquid formulation in the library was imaged by the visual inspection station. The captured images of the library are shown in FIG. 9. Formulations in Row A where there was no stabilizer all grew large crystals which settled to the bottom of the vials. As the amount of stabilizer is increased and as the molecular weight of the stabilizer is increased, formulations appeared homogeneous. Wells D3, D4, D5, and D6 were looked the most homogeneous by visual inspection.

Figure 11:
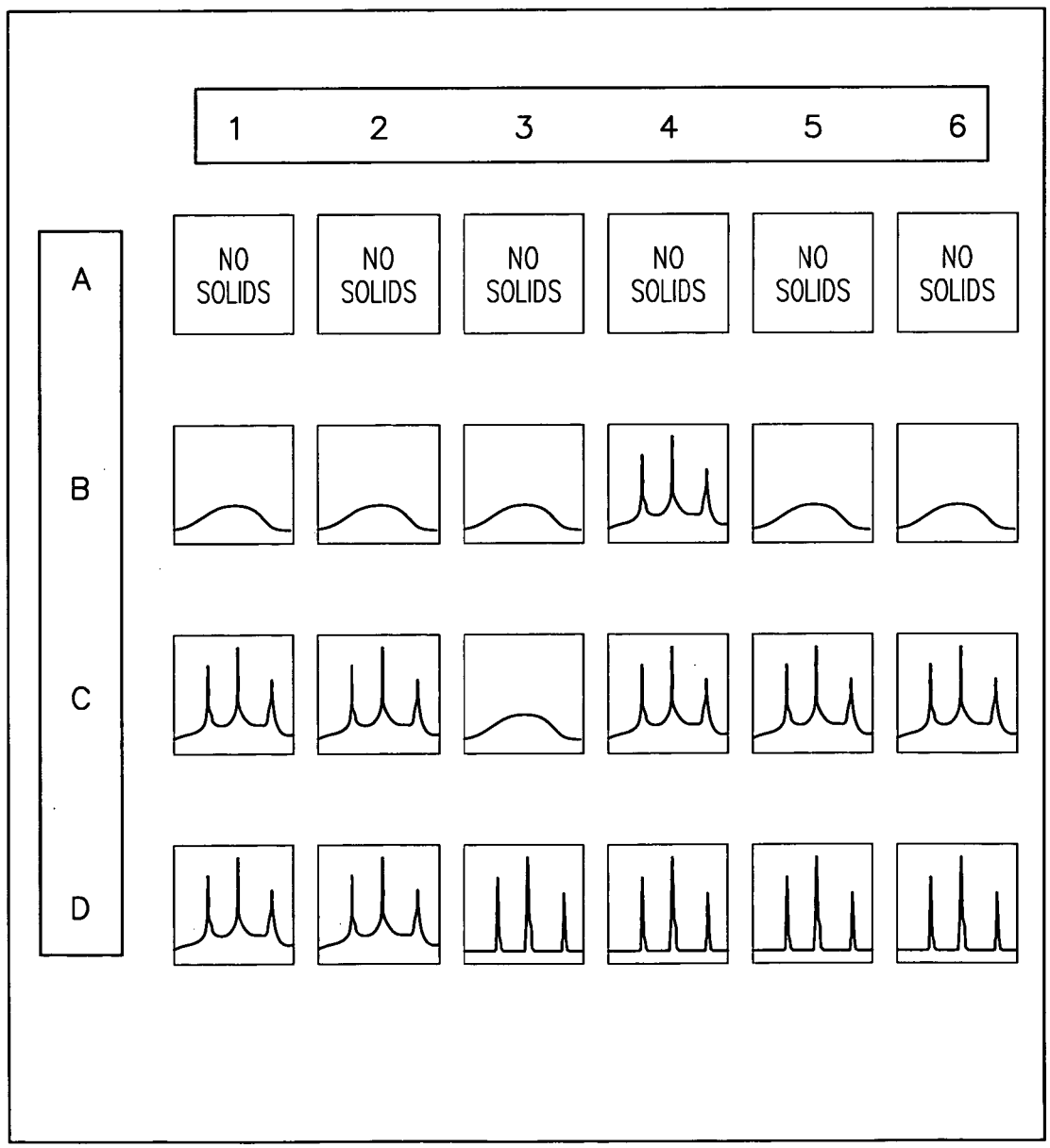
FIG. 11 shows a schematic of illustrative diffraction patterns and an illustrative table of corresponding calculated crystallinity for the selected formulations used in Example 2.

Based upon the data obtained from the visual inspection screening, the liquid handling robot of the formulation station was then used to daughter the selected formulations of the library for additional screenings. For each selected formulation, the liquid handling robot daughtered 400 uL to an array of vials for particle size screening, a sample to an array of 8 mL vials for dissolution screening, and 100 uL to an assembly holding a substrate for crystallinity screening. The substrate having samples thereon can be used for a variety of screening, including for example, birefringence, Raman, x-ray diffraction, or melting point, without handling of the individual sample materials. Representative crystallinity data is depicted in FIG. 11. Detailed description of the preferred substrate is provided in the PCT/US 02/16962, which is hereby now incorporated by reference. The volume of the dissolution sample was calculated by Library Studio® based on the concentration of the active compound so that 0.1 mg of the active compound was transferred into the dissolution sample.

Figure 10:
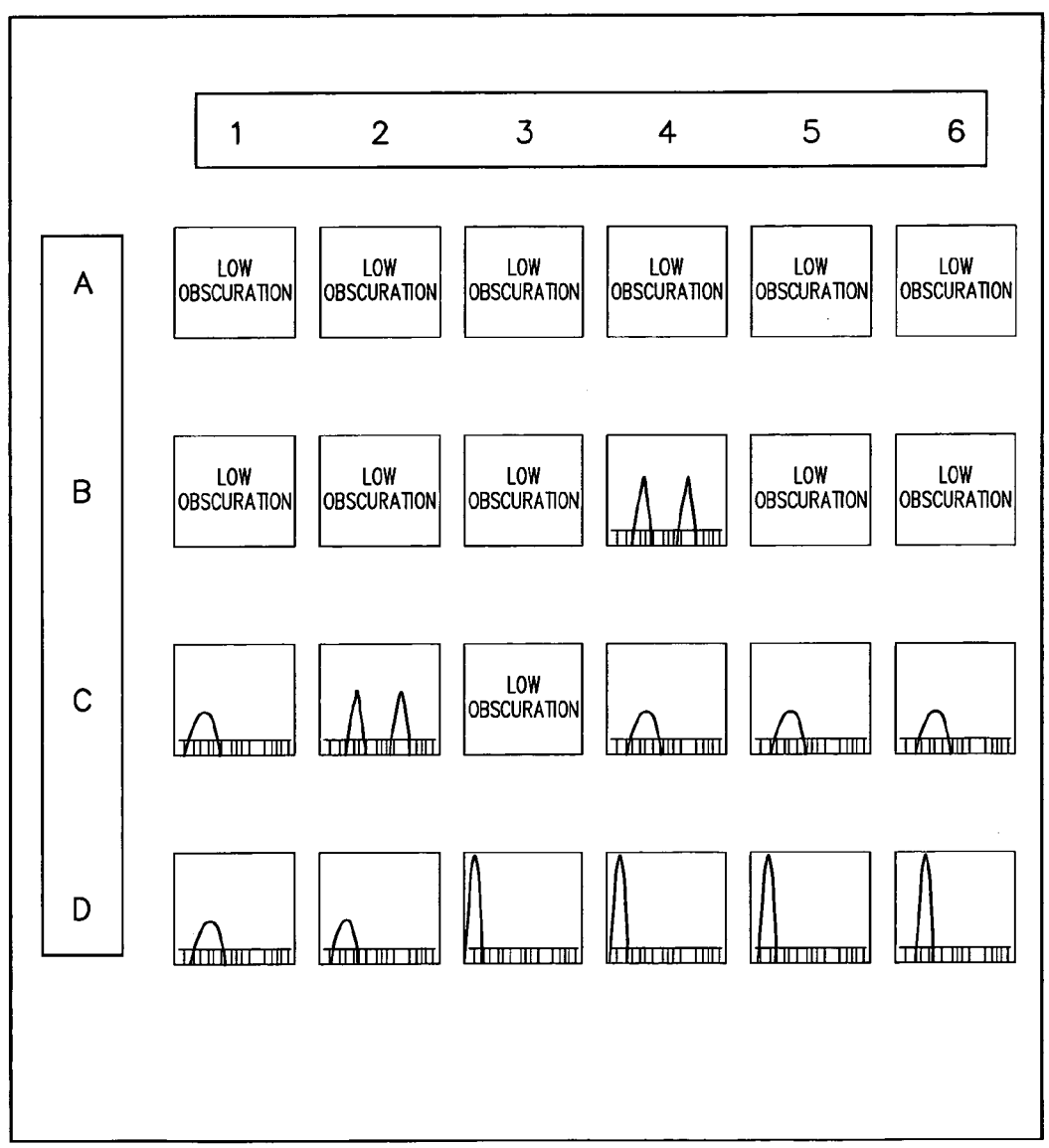
FIG. 10 shows a schematic of illustrative volume average particle size distributions of the selected formulations used in Example 2.

The 400 uL vials of selected formulations were transported to the particle size station comprising of a commercial multiangle light scattering instrument that has been implemented with a robotic autosampler. These vials were screened for particle size. Volume average particle size distributions are plotted in FIG. 10. Each graph shows the distribution from 0.1 um to 100 um on a logarithmic scale. B4 and C2 showed bimodal distributions of particle size. The smallest particle sizes were seen in well D4.

Figure 12:
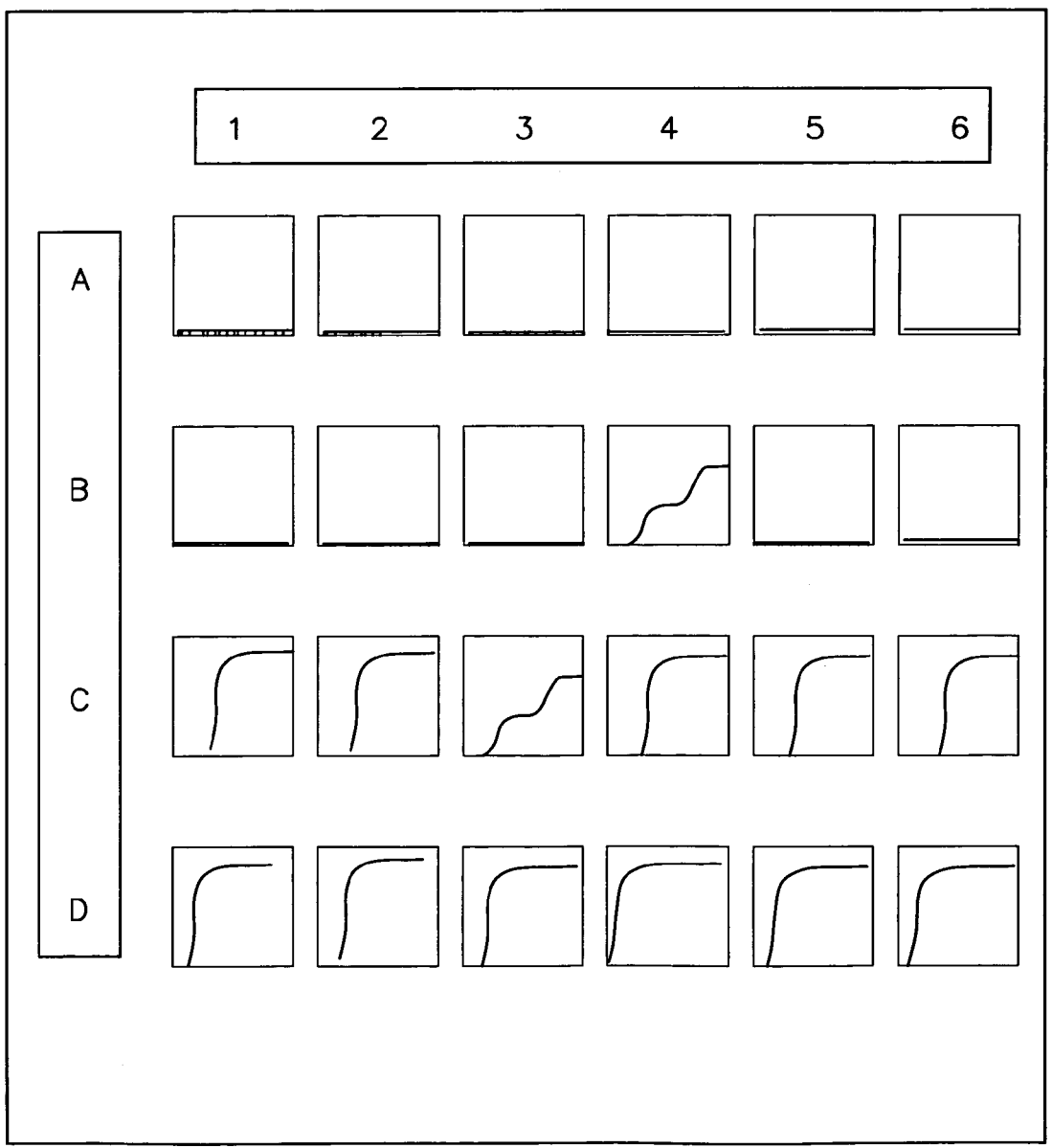
FIG. 12 shows a schematic of illustrative dissolution profiles and dissolution times of the selected formulations used in Example 2.

After freeze-drying and lyophylization, the array of 8 mL vials holding aliquots of selected formulations was transported to the solubility station for solubility screening using the high throughput solubility screening system and methods of the present invention described above. Dissolution profiles and dissolution times of the selected formulations are shown in FIG. 12.

As the data described above revealed, where there was no stabilizer, no stable formulations were formed. The data showed that as the relative amount of stabilizer was increased, the average particle size of the formulation decreased, the crystallinity increased, and the dissolution rate decreased. This workflow also showed that the fastest dissolution rate correlated with the smallest particle size and in this case the sample formulation with the highest crystallinity. In addition, wells B4 and C3 showed bimodal particle size distributions that correlated with dissolution profiles that showed two different dissolution rates in each sample formulation.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

We claim:

1. A method for determining a dissolution profile for a sample material, the method comprising
    dissolving at least a portion of the sample material in a solvent over a period of time to form a solution, the period of time defining a dissolution period, the solution having a concentration of the sample material that varies during the dissolution period,
    sampling a portion of the solution at least twice during the dissolution period, the solution being sampled at a first time within the dissolution period to obtain a first aliquot of the solution, and at a later second time within the dissolution period to obtain a second aliquot of the solution,
    subsampling a portion of the first aliqout of the solution to obtain a first sub-aliquot of the solution resulting in a remainder portion of the first aliquot,
    determining the concentration of the sample material in the first sub-aliquot of the solution,
    returning the remainder portion of the first aliquot to the solution,
    subsampling a portion of the second aliqout of the solution to obtain a second sub-aliquot of the solution resulting in a remainder portion of the second aliquot,
    determining the concentration of the sample material in the second sub-aliquot of the solution, and
    returning the remainder portion of the second aliquot to the solution.

2. The method of claim 1 further comprising
    providing a first make-up aliquot of a liquid media to the solution, the first make-up aliquot having a volume about the same as the volume of the first sub-aliquot, the first make-up aliquot being provided after sampling to obtain the first aliquot of the solution, and before sampling to obtain the second aliquot of the solution, and
    providing a second make-up aliquot of a liquid media to the solution, the second make-up aliquot having a volume about the same as the volume of the second sub-aliquot, the second make-up aliquot being provided after sampling to obtain the second aliquot of the solution.

3. The method of claim 2 wherein the liquid media for each of the first make-up aliquot and the second make-up aliquot is a solvent that is the same as the solvent in which at least a portion of the sample material is initially dissolved.

4. The method of claim 2 wherein the liquid media for each of the first make-up aliquot and the second make-up aliquot is a cosolvent that has a chemical composition that is different from the solvent in which at least a portion of the sample material is initially dissolved, whereby the solution has a solvent composition that varies over time during the dissolution period.

5. The method of claim 2 wherein the liquid media for each of the first make-up aliquot and the second make-up aliquot is pH-adjusting agent, whereby the solution has a pH that varies over time during the dissolution period.

6. The method of claim 1 wherein the solution is sampled at least three times during the dissolution period, the method further comprising
    sampling a portion of the solution at a third time within the dissolution period to obtain a third aliquot of the solution,
    subsampling a portion of the third aliquot of the solution to obtain a third sub-aliquot of the solution, and
    determining the concentration of the sample material in the third sub-aliquot of the solution,
    wherein the third time is after the second time.

7. The method of claim 6 wherein the sampling frequencies defined by the difference in time between the first time and the second time, and by the difference in time between the second time and the third time, are each not more than about 1 minute.

8. The method of claim 6 further comprising combining the sample material with the solvent at an initiation time, $t_o$, to initiate dissolution of the sample material in the solvent, wherein
    the first time at which the solution is sampled to obtain the first aliquot is within about 1 minute after the initiation time, $t_o$,
    the sampling frequencies defined by the difference in time between the first time and the second time, and by the difference in time between the second time and the third time, are each not more than about 1 minute.

9. The method of claim 8 wherein the solution is sampled at least six times during the dissolution period, the method further comprising
    sampling a portion of the solution at a fourth time within the dissolution period to obtain a fourth aliquot of the solution, subsampling a portion of the fourth aliquot of the solution to obtain a fourth sub-aliquot of the solution, and determining the concentration of the sample material in the fourth sub-aliquot of the solution,
    sampling a portion of the solution at a fifth time within the dissolution period to obtain a fifth aliquot of the solution, subsampling a portion of the fifth aliquot of the solution to obtain a fifth sub-aliquot of the solution, and determining the concentration of the sample material in the fifth sub-aliquot of the solution,
    sampling a portion of the solution at a sixth time within the dissolution period to obtain a sixth aliquot of the solution, subsampling a portion of the sixth aliquot of the solution to obtain a sixth sub-aliquot of the solution, and determining the concentration of the sample material in the sixth sub-aliquot of the solution,
    wherein the fourth time is after the third time, the fifth time is after the fourth time, and the sixth time is after the fifth time.

10. The method of claim 9 wherein the sampling frequencies defined by the difference in time between the fourth time and the fifth time, and by the difference in time between the fifth time and the sixth time, are each not more than about 1 minute.

11. The method of claim 10 wherein the solution is sampled at least six times over at least two distinct sampling intervals during the dissolution period, a first sampling interval comprising the first time, the second time and the third time, and a second sampling interval comprising the fourth time, the fifth time and the sixth time, the first and second sampling intervals being separated in time by a non-sampling interval during which no sampling of the solution occurs, the non-sampling interval being defined by a period of time having a duration not less than about two times the longest of the sampling frequencies.

12. The method of claim 1 wherein the sampling frequency defined by the difference in time between the first time and the second time is not more than about 1 minute.

13. The method of claim 1 further comprising combining the sample material with the solvent at an initiation time, $t_o$, to initiate dissolution of the sample material in the solvent, wherein the first time at which the solution is sampled to obtain the first aliquot is within about 1 minute after the initiation time, $t_o$.

14. The method of claim 13 wherein the first time at which the solution is sampled to obtain the first aliquot is within about 30 seconds after the initiation time, $t_o$.

15. The method of claim 13 wherein the first time at which the solution is sampled to obtain the first aliquot is within about 10 seconds after the initiation time, $t_o$.

16. The method of claim 1 wherein
the solution is sampled using an automated sampling probe, the sampling probe having a distal end and a proximate end, the distal end of the sampling probe being positionable in fluid communication with the solution in the sample container for sampling a portion of the solution to obtain sampled aliquots, the proximate end of the sampling probe being in fluid communication through a flow path with a sub-sampling device for obtaining the sub-sampled sub-aliquots,
the method further comprises filtering the first aliquot of the solution during or after sampling to obtain a filtered first aliquot of the solution, and filtering the second aliquot of the solution during or after sampling to obtain a filtered second aliquot of the solution, the sampled aliquots being filtered with an in-line filter integral with the sampling probe or in fluid communication with the proximate end of the sampling probe in the flow path providing fluid communication to the sub-sampling device,
the remainder portion of the first sub-aliquot and the remainder portion of the second sub-aliquot are returned from the sub-sampling device to the solution through the flow path and the sampling probe in a reverse flow direction, and
the remainder portions of the sub-aliquots backflush the in-line filter while being returned to the solution in the reverse flow direction.

17. The method of claim 1 wherein the sample material is a solid.

18. The method of claim 17 further comprising combining the solid sample material with the solvent to initiate dissolution and to form a dispersion comprising the solution and undissolved solid sample material dispersed in the solution.

19. The method of claim 18 wherein the dispersion is a substantially uniform dispersion.

20. The method of claim 1 wherein the sample material comprises a drug candidate.

21. The method of claim 20 wherein the sample material consists essentially of a drug candidate.

22. The method of claim 22 wherein the sample material comprises a drug composition comprising one or more drug candidates and one or more excipients.

23. The method of claim 1 further comprising combining not more than about 50 mg of the sample material with the solvent to initiate dissolution of the sample material in the solvent.

24. The method of claim 23 wherein not more than tout 20 mg of the sample material is combined with the solvent.

25. The method of claim 23 wherein not more than about 10 mg of the sample material is combined with the solvent.

26. The method of claim 23 wherein not more than about 5 mg of the sample material is combined with the solvent.

27. The method of claim 23 wherein not more than tout 2 mg of the sample material is combined with the solvent.

28. The method of claim 23 wherein not more than about 1 mg of the sample material is combined with the solvent.

29. The method of claim 23 wherein not more than about 0.5 mg of the sample material is combined with the solvent.

30. The method of claim 23 wherein the sample material is combined with an amount of solvent effective for forming a solution having a detectable concentration of sample material in the solution.

31. The method of claim 23 wherein the sample material is combined with an amount of solvent effective for forming solution having a concentration of sample material in the solution ranging from about 0.01 mg/ml to about 10 mg/ml.

32. The method of claim 23 wherein an amount of sample material ranging from 0.01 mg to 0.5 mg is combined with an amount of solvent ranging from 1 ml to 10 ml.

33. The method of claim 1 wherein the surface area of the sample material is known or determined, the method further comprising determining an intrinsic dissolution rate for the sample material for one or more times during the dissolution period.

34. The method of claim 1 wherein the sample material is a first sample material, the method further comprising
repeating each step of the method for at least one other distinct second sample material, and
comparing a relative dissolution rate for the first sample material and the second sample material for one or more times during the dissolution period.

35. The method of claim 1 further comprising generating a data set that defines the dissolution profile, the data set being generated by a protocol that comprises
defining a first data point of the dissolution profile by associating the determined concentration of sample material in the first aliquot with the first time, and
defining a second data point of the dissolution profile by associating the determined concentration of sample material in the second aliquot with the second time.

36. The method of claim 1 wherein the sample material is a one member of an array of sample materials, the method further comprising
repeating each step of the method for at least one other member of the array.

37. The method of claim 36 wherein the array of sample materials comprises four or more sample materials, the method further comprising for each of the four or more sample materials,
combining the sample material with the solvent in an individual, separate container, the container for each of the four or more sample materials being selected from four or more containers that are formed in or supported on a common substrate.

38. The method of claim 36 wherein for each of the four or more sample materials,
at least one of the sample material or the solvent are provided to the container by an automated dispensing probe at the initiation time, $t_o$, and the solution is sampled at the first time to obtain the first aliquot using an automated sampling probe.

39. The method of claim 36 wherein the array of sample materials comprises four or more sample materials, each of the four or more sample materials having a chemical composition that is different from each other.

40. The method of claim 36 wherein the array of sample materials comprises two or more sample materials, each of the two or more sample materials having a crystalline structure different from each other.

41. The method of claim 36 wherein the array of sample materials comprises two or more sample materials, each of the two or more sample materials having the same chemical composition and having a crystalline structure different from each other.

42. The method of claim 36 wherein the ray of sample materials comprises four or more sample materials that are substantially the same, the method further comprising combining each of the four or more sample materials with a different dissolution environment.

43. A method for determining a dissolution profile for a sample material, the method comprising dissolving at least a portion of the sample material in a solvent over a period of time to form a solution, the period of time defining a dissolution period, the solution having a concentration of the sample material that varies during the dissolution period, the dissolving including combining the sample material with the solvent in a container to initiate dissolution of the sample material in the solvent, at least one of the sample material or the solvent being provided to the container by an automated dispensing probe at an initiation time, $t_o$, using an automated sampling probe for sampling the solution at least twice during the dissolution period, the solution being sampled at a first time within the dissolution period to obtain a first aliquot of the solution, and at a later second time within the dissolution period to obtain a second aliquot of the solution, subsampling a portion of the first aliqout of the solution to obtain a first sub-aliquot of the solution, determining the concentration of the sample material in the first sub-aliquot of the solution, subsampling a portion of the second aliqout of the solution to obtain a second sub-aliquot of the solution, and determining the concentration of the sample material in the second sub-aliquot of the solution.

44. The method of claim 43 further comprising controlling the dispensing probe independently of the sampling probe.

45. A method for determining a dissolution profile for a sample material, the method comprising dissolving at least a portion of the sample material in a solvent over a period of time to form a solution, the period of time defining a dissolution period, the solution having a concentration of the sample material that varies during the dissolution period, sampling a portion of the solution at least twice during the dissolution period, the solution being sampled at a first time within the dissolution period to obtain a first aliquot of the solution, and at a later second time within the dissolution period to obtain a second aliquot of the solution, including filtering the first aliquot of the solution during or after sampling to obtain a filtered first aliquot of the solution, and filtering the second aliquot of the solution during or after sampling to obtain a filtered second aliquot of the solution, subsampling a portion of the first aliquot of the solution to obtain a first sub-aliquot of the solution, determining the concentration of the sample material in the first sub-aliquot of the solution, subsampling a portion of the second aliquot of the solution to obtain a second sub-aliquot of the solution, and determining the concentration of the sample material in the second sub-aliquot of the solution.

46. The method of claim 45 wherein the solution is sampled using an automated sampling probe, the sampling probe having a distal end and a proximate end, the distal end of the sampling probe being positionable in fluid communication with the solution in the sample container for sampling a portion of the solution to obtain sampled aliquots, and the sampled aliquots are filtered with an in-line filter integral with the sampling probe or in fluid communication with the proximate end of the sampling probe.

47. A method for determining a dissolution profile for a sample material, the method comprising dissolving at least a portion of the sample material in a solvent over a period of time to form a solution, the period of time defining a dissolution period, the solution having a concentration of the sample material that varies during the dissolution period, the dissolving including varying a property of the solvent over time during the dissolution period, sampling a portion of the solution at least twice during the dissolution period, the solution being sampled at a first time within the dissolution period to obtain a first alipuot of the solution, and at a later second time within the dissolution period to obtain a second aliquot of the solution, subsampling a portion of the first aliquot of the solution to obtain a first sub-aliquot of the solution, determining the concentration of the sample material in the first sub-aliquot of the solution, subsampling a portion of the second aliquot of the solution to obtain a second sub-aliquot of the solution, and determining the concentration of the sample material in the second sub-aliquot of the solution.

48. The method of claim 47 further comprising varying the chemical composition of the solvent over time during the dissolution period.

49. The method of claim 47 further comprising varying the pH of the solvent over time during the dissolution period.

50. The method of claim 47 further comprising varying the temperature of the solvent over time during the dissolution period.

51. A method for generating data defining a dissolution profile for a sample material, the method comprising dissolving at least a portion of the sample material in a solvent over a period of time to form a solution, the period of time defining a dissolution period, the solution having a concentration of the sample material that varies during the dissolution period, sampling a portion of the solution at a first time within the dissolution period to obtain a first aliquot of the solution, subsampling a portion of the first aliquot of the solution to obtain a first sub-aliquot of the solution, such subsampling thereby also resulting in a remainder portion of the first aliquot, returning the remainder portion of the first aliquot to the solution, sampling a portion of the solution at a later second time within the dissolution period after the remainder portion of the first aliquot is returned to the solution, to obtain a second aliquot of the solution, subsampling a portion of the second aliquot of the solution to obtain a second sub-aliquot of the solution, such subsampling thereby also resulting in a remainder portion of the second aliquot, returning the remainder portion of the second aliquot to the solution, determining the concentration of the sample material in the first sub-aliquot of the solution, whereby a first data point of the dissolution profile is defined by association of the concentration determined in the first sub-aliquot with the first time, and determining the concentration of the sample material in the second sub-aliquot of the solution, whereby a second data point of the dissolution profile is defined by association of the concentration determined in the second sub-aliquot with the second time.

52. The method of claim 51 further comprising providing a first make-up aliquot of a liquid media to the solution, the first make-up aliquot having a volume about the same as the volume of the first sub-aliquot, the first make-up aliquot being provided after sampling to obtain the first aliquot of the solution, and before sampling to obtain the second aliquot of the solution, and providing a second make-up aliquot of the liquid media to the solution, the second make-up aliquot having a volume about the same as the volume of the second sub-aliquot, the second make-up aliquot being provided after sampling to obtain the second aliquot of the solution.

53. A system for determining a dissolution profile for a sample material, the system comprising a sample container for dissolving at least a portion of the sample material in a solvent over a dissolution period of time to form a solution that has a concentration of the sample material that varies during the dissolution period, an automated sampling probe for sampling a portion of the solution at least twice during the dissolution period, the solution being sampled at first and second times within the dissolution period to obtain fist and second aliquots of the solution, respectively, the sampling probe having a distal end positionable in fluid communication with the solution in the sample container, and having a proximate end, a sub-sampling device including a sampling valve in fluid communication with the proximate end of the sampling probe, the sub-sampling device being configured for subsampling a portion of each of the first and second aliquots of the solution to obtain first and second sub-aliquots of the solution, and an analytical unit for determining the concentration of the sample material in the first and second sub-aliquots of the solution.

54. The system of claim 53 further comprising an automated dispensing probe for providing the sample material to the container.

55. The system of claim 53 further comprising an automated dispensing probe for providing the sample material to the container, and a control system for independently controlling the automated sampling probe and the automated dispensing probe.

56. The system of claim 53 further comprising a microprocessor having automation software for controlling the automated sampling probe and the sub-sampling device.

57. The system of claim 53 further comprising an in-line filter for filtering the first and second aliquots of the solution during or after sampling to obtain filtered first and second aliquots of the solution, respectively, the in-line filter being integral with the sampling probe or in fluid communication with the proximate end of the sampling probe in the flow path providing fluid communication to the sub-sampling device.

58. The system of claim 53 wherein the automated sampling probe is a component of an automated liquid handling system, the liquid-handling system further comprising a robotic arm for translating the automated sampling probe, and a pump in continuous or selectable fluid communication with the sampling probe for providing a motive force for withdrawing a portion of the solution into the probe to effect sampling.

59. The system of claim 58 wherein the pump is a positive displacement pump.

60. The system of claim 58 wherein the pump is a reciprocating pump.

61. The system of claim 58 wherein the pump is a syringe pump.

62. The system of claim 58 wherein the pump is in fluid communication with the sampling valve such that the sampling valve provides continuous or selectable fluid communication between the pump and the proximate end of the sampling probe, and the analytical unit comprises a detector in fluid communication with the sampling valve.

63. The system of claim 62 wherein the sampling valve comprises a sample loop, and the sampling valve is configured so that in a first selectable position, the pump is in fluid communication with the proximate end of the sampling probe through a flow path that includes the sample loop, and so that in a second selectable position, the pump is in fluid communication with the proximate end of the sampling probe through a flow path that bypasses the sample loop.

64. The system of claim 63 further comprising an in-line filter for filtering the first and second aliquots of the solution during or after sampling to obtain filtered first and second aliquots of the solution, respectively, the in-line filter being integral with the sampling probe or in fluid communication with the proximate end of the sampling probe in the flow path providing fluid communication to the sampling valve, such that when the sampling valve is in the first selectable position, at least part of the filtered sampled aliquot is loaded into the sample loop, and such that when the sampling valve is in the second selectable position, a remainder portion of the filtered sampled aliquot not loaded into the sample loop is returned to the solution in a reverse flow direction through the flow path that bypasses the sample loop and backflushes the in-line filter.

65. The system of claim 62 wherein the sampling valve comprises a sample loop, and the sampling valve is configured so that in a first selectable position, the sample loop is selectably aligned to a sampling flow pat for loading at least part of the sampled aliquot into the sample loop, and so that in a second selectable position, the sample loop is selectably aligned to a detection flow path for discharging the contents the sample loop as a sub-aliquot of the sampled aliquot to the detector.

66. The system of claim 62 wherein the pump is a first pump and the sampling valve is a multi-port sampling valve comprising a sample loop, the sampling valve being configured in a first selectable position for loading at least part of the sampled aliquot into the sample loop through a sampling flow path from the proximate end of sampling probe to the first pump, the sampling valve being configured in a second selectable position for returning a remainder portion of the sampled aliquot not loaded into the sample loop to the container through a remainder-return flow path from the first pump to the proximate end of the sampling probe, and the sampling valve being further configured in one of the selectable positions for discharging the contents the sample loop as a sub-aliquot of the sampled aliquot through a detection flow path from a second pump to the detector.

67. The system of claim 62 wherein the pump is a first pump and the sampling valve is a multi-port sampling valve comprising a first sample loop and a second sample loop, the sampling valve being configured in a first selectable position for loading at least part of the sampled aliquot into the first sample loop through a sampling flow path from the proximate end of sampling probe to the first pump, the sampling valve being configured in the second selectable position for returning a remainder portion of the sampled aliquot not loaded into the first sample loop to the container through a remainder-return flow path from the first pump to the proximate end of the sampling probe, the sampling valve being further configured in the second selectable position for loading a make-up liquid media into the first sample loop and simultaneously advancing the contents of the first sample loop to a second sample loop, the sampling valve being further configured in the first selectable position for discharging the contents the second sample loop as a sub-aliquot of the sampled aliquot through a detection flow path from a second pump to the detector, the sampling valve being further configured in the first selectable position for providing the make-up liquid media loaded into the first sample loop as a make-up aliquot through a make-up flow path from a third pump to the proximate end of the sampling probe for delivery to the solution in the container.

68. The system of claim 62 wherein the analytical unit further comprises a separation device in fluid communication with the sampling valve and with the detector, the separation device being adapted for separating one or more components of the subsampled sub-aliquots discharged from the sampling valve from other components thereof, the detector being adapted for detecting a property of the one or more separated components.

69. The system of claim 68 wherein the separation device is a liquid chromatography column.

70. The system of claim 68 wherein the separation device is a liquid chromatography column, and the detector is selected from one or more of a light-scattering detector, a refractive index detector, a fluorescence detector, an infrared detector, and a spectroscopic detector.

71. The system of claims 53 or 62 wherein the analytical unit comprises a flow detector in fluid communication with the sub-sampling device.

72. The system of claims 53 or 62 wherein the analytical unit further comprises a separation device in fluid communication with the sub-sampling device.

73. The system of claims 53 or 62 wherein the analytical unit comprises a liquid chromatography system or a flow-injection analysis system.

* * * * *

UNITED STATES PATENT AND TRADEMARK OFFICE
CERTIFICATE OF CORRECTION

PATENT NO.       : 7,024,955 B2                                  Page 1 of 1
APPLICATION NO.  : 10/414185
DATED            : April 11, 2006
INVENTOR(S)      : Carlson et al.

It is certified that error appears in the above-identified patent and that said Letters Patent is hereby corrected as shown below:

On the Cover Page, Item (56) References Cited, U.S. PATENT DOCUMENTS, the following should read:

3,846,075  A  *  11/1974  Cioffi..........................23/253

Col. 35, Line 65, replace "22" with --20-- between "claim" and "wherein"

Col. 36, Line 11, replace "tout" with --about--

Col. 37, Line 16, replace "ray" with --array--

Col. 39, Line 47, replace "fist" with --first--

Col. 40, Line 62, replace "pat" with --path--

Signed and Sealed this

Eleventh Day of July, 2006

JON W. DUDAS
*Director of the United States Patent and Trademark Office*